US011348668B2

(12) United States Patent
Atreja et al.

(10) Patent No.: US 11,348,668 B2
(45) Date of Patent: May 31, 2022

(54) SYSTEMS AND METHODS FOR IDENTIFYING, RANKING, AND PRESCRIBING HEALTH CARE APPLICATIONS

(71) Applicant: Icahn School of Medicine at Mount Sinai, New York, NY (US)

(72) Inventors: Ashish Atreja, New York, NY (US); Jason Rogers, New York, NY (US)

(73) Assignee: ICAHN SCHOOL OF MEDICINE AT MOUNT SINAI, New York, NY (US)

(*) Notice: Subject to any disclaimer, the term of this patent is extended or adjusted under 35 U.S.C. 154(b) by 95 days.

(21) Appl. No.: 16/078,618

(22) PCT Filed: Feb. 17, 2017

(86) PCT No.: PCT/US2017/018509
§ 371 (c)(1),
(2) Date: Aug. 21, 2018

(87) PCT Pub. No.: WO2017/151331
PCT Pub. Date: Sep. 8, 2017

(65) Prior Publication Data
US 2019/0051388 A1    Feb. 14, 2019

Related U.S. Application Data

(60) Provisional application No. 62/302,145, filed on Mar. 1, 2016.

(51) Int. Cl.
*G16H 10/60* (2018.01)
*G16H 20/10* (2018.01)
(Continued)

(52) U.S. Cl.
CPC ........... *G16H 10/60* (2018.01); *G06F 16/951* (2019.01); *G16H 20/10* (2018.01); *G16H 40/67* (2018.01); *G16H 50/30* (2018.01); *G16H 70/00* (2018.01)

(58) Field of Classification Search
CPC ...... G16H 10/60; G16H 50/30; G06F 16/951; G06F 19/324; G06Q 50/22
See application file for complete search history.

(56) References Cited

U.S. PATENT DOCUMENTS 9,836,545 B2 * 12/2017 LuVogt .................. G06Q 30/02
10,152,761 B2 * 12/2018 Kress ..................... G06Q 10/10
(Continued)

FOREIGN PATENT DOCUMENTS

KR    10-2002-0010293 A    2/2002
KR    10-2015-0075589 A    7/2015

OTHER PUBLICATIONS

Boudreaux et al., Evaluating and selecting mobile health apps: strategies for healthcare providers and healthcare organizations, TBM: Practice Tool 363-371 (Year: 2014).*
(Continued)

*Primary Examiner* — Evangeline Barr
*Assistant Examiner* — Jordan L Jackson

(57) ABSTRACT

Systems and methods are provided for identifying one or more health care applications in which a search request is received from a user at a remote client device. The request comprises an alphanumeric query and filtering criteria. A plurality of applications is searched to identify applications that satisfy the filtering criteria and further match the alphanumeric query thereby identifying a set of matching applications. Each respective application in the plurality of applications is (i) for a clinical indication and (ii) includes an evidence score generated by health care providers. The search query response is formatted for display by sorting the
(Continued)

matching applications by sorting criteria thereby forming a sorted list of matching applications. At least a portion of the sorting criteria is the evidence score. The search query response, including the sorted list of matching applications, is communicated to the remote client device.

17 Claims, 15 Drawing Sheets

(51) Int. Cl.
    *G16H 40/67*     (2018.01)
    *G16H 70/00*     (2018.01)
    *G16H 50/30*     (2018.01)
    *G06F 16/951*     (2019.01)

(56) References Cited

U.S. PATENT DOCUMENTS

| | | | |
|---|---|---|---|
| 2009/0083067 A1 | 3/2009 | Freeland et al. | |
| 2013/0066650 A1* | 3/2013 | Ackerman | G06Q 30/0631 705/2 |
| 2014/0244296 A1* | 8/2014 | Linn | G16H 40/20 705/3 |
| 2015/0347688 A1 | 12/2015 | Miller | |
| 2016/0042431 A1* | 2/2016 | Douglass | G16H 50/70 705/3 |
| 2016/0357794 A1* | 12/2016 | Liang | G06F 16/957 |

OTHER PUBLICATIONS

RX iPrescribeApps, iMedicalApps (Jan. 9, • RX iPrescribeApps, iMedicalApps (Jan. 9, 2016) (Year: 2016).*

International Search Report and Written Opinion for International Patent Application No. PCT/US2017/018509, dated May 11, 2017, 15 pages.
Bishop et al., "Impact of Automated Digital Navigation Program on Bowel Preparation Quality and Patient Satisfaction for Colonoscopy: A Comparative Study Across Multiple Sites," iproc 2019;5(1):e15270.
Galsky et al., "A Web-Based Tool to Facilitate Shared Decision-Making Regarding Neoadjuvant Chemotherapy Use in Muscle-Invasive Bladder Cancer," iproc 2017;3(1):e43.
Kelly et al., "Fecal Microbiota Transplantation Is Highly Effective in Real-World Practice: Initial Results From the FMT National Registry," Gastroenterology. Jan. 2021; 160(1): 183-192.e3.
Krouss et al., "Project TOPS: Team-Based Oversight of Patient Satisfaction Through Real-Time Interdisciplinary Feedback," Jt Comm J Qual Patient Saf. Jul. 2020;46(7):427-430.
Makhni et al., "Usability and Learnability of RxUniverse, an Enterprise-Wide App Prescribing Platform Used in an Academic Tertiary Care Hospital," AMIA Annu Symp Proc. 2017; 1225-1232.
Otobo et al., "Reinventing Inflammatory Bowel Disease (IBD) Clinical Trial Recruitment Using Novel Digital Medicine Tools," iproc 2018;4(2):e11815.
Park et al., "Impact on Readmission Reduction Among Heart Failure Patients Using Digital Health Monitoring: Feasibility and Adoptability Study," JMIR Med Inform. Oct.-Dec. 2019 7(4): e13353.
Rogers et al., "Developing and Implementing a Digital Navigation Program to Improve Outcomes for Medicare Bundle Patients Undergoing Joint Replacement Surgery," iproc 2019;5(1):e15197.
Solad et al., "A Novel Digital Platform Approach to Enhance Enterprise-Wide Patient Portal Adoption," iproc 2018;4(2):e11816.
Szigethy et al., "White Paper AGA: The Impact of Mental and Psychosocial Factors on the Care of Patients With Inflammatory Bowel Disease," Clin Gastroenterol Hepatol. Jul. 2017;15(7):986-997.

* cited by examiner

502 — A method comprising, at a computer system having one or more processors and memory storing one or more programs to be executed by the one of more processors to perform the method, identifying one or more health care applications. Receive a search request from a user at a remote client device. The search request comprises an alphanumeric query and a set of filtering criteria.

504 — The set of filtering criteria (i) includes an indication that the evidence score of each respective health care application in the set of matching health care applications is to exceed a minimum threshold value and (ii) provides a value for this minimum threshold value.

506 — The set of filtering criteria includes a requirement that each respective health care application in the set of matching health care applications is approved by a governing body (e.g., the United States Food and Drug Administration).

508 — The set of filtering criteria includes a requirement that each respective health care application in the set of matching health care applications provides a direct link (e.g., is a two way direct link, a one way direct link, or a partial direct link) to an electronic health record system.

510 — The set of filtering criteria includes a requirement regarding a cost of each respective health care application in the set of matching health care applications.

512 — The set of filtering criteria includes a requirement regarding a characteristic of the intended end user of each respective health care application in the set of matching health care applications (e.g., the intended user is a (a) patient, (b) a provider, (c) a patient or provider, or (d) a health care team.

513 — The remote client device is a tablet or a smart phone.

514 — The user is not an author and is not associated with the health care applications.

515 — A health care application is ranked by individual members of a medical community thereby forming an overall ranking for the health care application that is distinct from the evidence score for the health care application (e.g., and is included in the search query response).

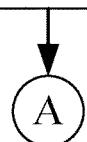

Fig. 5A

516 — Search a plurality of health care applications to identify health care applications in the plurality of health care applications that satisfy each filtering criterion in the set of filtering criteria and further match the alphanumeric query thereby identifying a set of matching health care applications. Each respective health care application in the plurality of health care applications is (i) for a clinical indication and (ii) includes an evidence score that is generated by a plurality of health care providers and not end users.

517 — The clinical indication of a health care application in the set of matching health care applications is a chronic gastrointestinal indication (e.g., inflammatory bowel disease, obesity, irritable bowel syndrome, gastrointestinal neoplasia, Celiac disease, a food allergy, or a food intolerance).

518 — The clinical indication of a health care application in the set of matching health care applications is a disease.

520 — The clinical indication of a health care application in the set of matching health care applications is an allergy.

522 — The clinical indication of a health care application in the set of matching health care applications is a cancer (e.g., liver cancer, breast cancer, brain cancer, colon cancer, pancreatic cancer, lung cancer, stomach cancer, bone cancer, or a leukemia).

524 — The clinical indication of a health care application in the set of matching health care applications is a disorder of the brain or nervous system.

526 — The clinical indication of a health care application in the set of matching health care applications is an eye disorder, an ear disorder, or a heart disorder.

528 — The clinical indication of a health care application in the set of matching health care applications is a heart or circulation disorder.

530 — The clinical indication of a health care application in the set of matching health care applications is a blood disorder, a disorder of the urinary tract, a hormonal disorder, a muscle disorder, a bone disorder, or a joint disorder.

Fig. 5B

Format for display a search query response. The search query response includes an identification of each respective health care application in the set of matching health care applications. The formatting includes sorting the set of matching health care applications by sorting criteria thereby forming a sorted list of matching health care applications. At least a portion of the sorting criteria is the evidence score.

― 534

― 536

> Access a list of favorite health care applications in a user profile associated with the user. Place each health care application in the set of matching health care applications that is also in the list of favorite health care applications at the beginning of the sorted list of matching health care applications.

― 538

> Access a list of prescribed health care applications in a user profile associated with the user. The user has prescribed each respective health care application in the list of prescribed health care applications to at least one patient. The formatting further comprises placing each health care application in the set of prescribed health care applications that is also in the set of matching health care applications at the beginning of the sorted list of matching health care applications.

― 540

Communicate the search query response including the sorted list of matching health care applications to the remote client device.

― 542

> Receive a favorite health care application request from the user at the remote client device. Obtain, from a user profile associated with the user, a first subset of health care applications in the plurality of health care applications. The user has designated each respective heath care application in the first subset of heath care applications as a favorite health care application. Communicate the first subset of health care applications to the remote client device.

544 — Receive a prescription request from the user at the remote client device. The prescription request comprises (i) an identification of a first health care application in the sorted list of matching health care applications from the user at the remote client device and (ii) an identification of the patient associated with the user. Responsive to receiving the identification, send an invitation to use the first health care application to an electronic address associated with the patient.

546 — The electronic address associated with the patient is obtained, without user intervention, from an electronic medical record associated with the patient, in response to receiving the prescription request.

548 — The identification of the patient associated with the user includes the electronic address associated with the patient 550 — Store an indication that the user has prescribed the first health care application to a patient in a user profile associated with the user.

552 — Receive a prescription history request from the user at the remote client device. Obtain, from a user profile associated with the user, a second subset of health care applications in the plurality of health care applications. The user has prescribed each respective heath care application in the second subset of heath care applications to one or more patients. Communicate the prescription history information, for the user for the second subset of health care applications, to the remote client device.

554 — Communicate to the remote client device, for each respective health care application in the second subset of health care applications, (i) an identity of each patient the respective health care application was prescribed to by the user, (ii) an indication for each respective patient whether the patient downloaded and used the respective health care application, and (iii) a date the respective health care application was prescribed to the respective patient by the respective user.

556 — The prescription history information for the user is sortable by any one combination of (i) health care application name, (ii) patient name, (iii) prescription date, and (iv) whether or not the respective health care application has been downloaded by the patient.

SYSTEMS AND METHODS FOR IDENTIFYING, RANKING, AND PRESCRIBING HEALTH CARE APPLICATIONS

CROSS REFERENCE TO RELATED APPLICATIONS

This Application is a National Stage of International Patent Application No. PCT/US2017/018509, entitled "Systems and Methods for Identifying, Ranking, and Prescribing Health Care Applications," filed Feb. 17, 2017 and published as WO 2017/151331 A1, which claims priority to U.S. Provisional Patent Application No. 62/302,145 entitled "Systems and Methods for Identifying, Ranking, and Prescribing Health Care Applications," filed Mar. 1, 2016, each of which is hereby incorporated by reference.

TECHNICAL FIELD

The present disclosure relates generally to systems and methods for providing a platform in which medical practitioners can search and browse for evidence-based digital medicine applications, rate them, and prescribe them to patients.

BACKGROUND

Any perusal of the medical category within the APPLE APP STORE and related venues will reveal that there is a vast array of applications available for downloading. These applications range from applications to facilitate ordering contact lenses to applications to track pregnancy or check depression. Moreover, these applications are often ranked by customer rating scores. While each of these applications, and the venues that offer them, are important advancements in their own right, they have drawbacks from the medical practitioner perspective. In particular, while customer rating scores have commercial importance, the medical practitioner, seeking applications for patients, is also interested in the state of scientific evidence surrounding the design, efficacy, and implementation behind such applications, in other words, an evidence score for such applications. Such an evidence score is not available for such applications. Moreover, the medical practitioner cannot filter the applications at such venues by filtering criteria, such as whether such applications have been approved by a governing body such as the United States Food and Drug Administration or whether such applications are linked to electronic medical records. Finally, there is no convenient mechanism within such venues for the medical practitioner to prescribe such applications to patients and to track whether patients actually use prescribed applications. Given this background, what is needed in the art are systems and methods for providing a forum to medical practitioners in which they can browse applications for clinical applications that have been assigned evidence based scores.

SUMMARY

The present disclosure addresses the need in the art for systems and methods for providing a forum to medical practitioners in which they can browse applications for clinical applications that have been assigned evidence based scores by medical practitioners, rather than end users. As such, the disclosed systems and methods are optimized for medical practitioners. Through the disclosed systems and methods, medical practitioners can browse applications based on numerous filtering criteria, select medical applications as favorites, and prescribe these applications to patients. Moreover, medical practitioners can maintain a profile of their favorite and prescribed application and records of who they prescribed such applications to and whether their prescribed patients actually use the applications.

One aspect of the present disclosure provides a method comprising, at a computer system having one or more processors and memory storing one or more programs to be executed by the one of more processors, to perform the method, identifying one or more health care applications by receiving a search request from a user at a remote client device (e.g., a tablet or a smart phone). The search request comprises an alphanumeric query and a set of filtering criteria. A plurality of health care applications is searched to identify health care applications in the plurality of health care applications that satisfy each filtering criterion in the set of filtering criteria and further match the alphanumeric query. This results in the identification of a set of matching health care applications. Each respective health care application in the plurality of health care applications is (i) for a clinical indication and (ii) includes an evidence score that is generated by a plurality of health care providers and not end users. A search query response is formatted for display. The search query response includes an identification of each respective health care application in the set of matching health care applications. The formatting includes sorting the set of matching health care applications by sorting criteria thereby forming a sorted list of matching health care applications. At least a portion of the sorting criteria is the evidence score. The search query response, including the sorted list of matching health care applications, is communicated to the remote client device.

Another aspect of the present disclosure provides a method comprising, at a computer system having one or more processors and memory storing one or more programs to be executed by the one of more processors to perform the method, identifying one or more health care applications by obtaining a search request within a first application running on the computer system from a user. The search request comprises an alphanumeric query and a set of filtering criteria. The search request is communicated to a remote server computer. A search query response is received from the remote server computer. The search query response includes an identification of each respective health care application in a set of matching health care applications from the remote server computer responsive to the search request. The set of matching health care applications (i) are in a plurality of health care applications curated at the remote server computer, (ii) satisfy each filtering criterion in the set of filtering criteria and (iii) match the alphanumeric query. Each respective health care application in the plurality of health care applications is (i) for a clinical indication and (ii) includes an evidence score that is generated by a plurality of health care providers and not end users. The search query response is displayed. This displaying includes displaying the set of matching health care applications as a list of health care applications that has been sorted by sorting criteria, where at least a portion of the sorting criteria is the evidence score.

In some embodiments, the set of filtering criteria (i) includes an indication that the evidence score of each respective health care application in the set of matching health care applications is to exceed a minimum threshold value and (ii) provides a value for this minimum threshold value.

In some embodiments, the set of filtering criteria includes a requirement that each respective health care application in the set of matching health care applications is approved by a governing body, such as the United States Food and Drug Administration.

In some embodiments, the set of filtering criteria includes a requirement that each respective health care application in the set of matching health care applications provides a direct link (e.g., a two-way direct link, a one-way direct link, or a partial direct link) to an electronic health record system.

In some embodiments, the set of filtering criteria includes a requirement regarding a cost of each respective health care application in the set of matching health care applications. For instance, that the application be free to users, or cost less than a threshold amount.

In some embodiments, the set of filtering criteria includes a requirement regarding a characteristic of the intended end user of each respective health care application in the set of matching health care applications. Examples of such characteristics includes whether the intended end user is (a) a patient, (b) a provider, (c) a patient or a provider, or (d) a health care team.

In some embodiments, the method further comprises accessing a list of favorite health care applications in a user profile associated with the user. In such embodiments, each health care application in the set of matching health care applications that is also in the list of favorite health care applications is placed at the beginning of the sorted list of matching health care applications.

In some embodiments, the method further comprises receiving a favorite health care application request from the user and obtaining, from a user profile associated with the user, a first subset of health care applications in the plurality of health care applications, where the user has designated each respective heath care application in the first subset of heath care applications as a favorite health care application. In such embodiments, the first subset of health care applications is communicated to the user.

Another aspect of the present disclosure comprises receiving a prescription request from the user, the prescription request comprising (i) an identification of a first health care application in the sorted list of matching health care applications and (ii) an identification of the patient associated with the user. Responsive to receiving the identification, an invitation to use the first health care application is sent to an electronic address associated with the patient. In some embodiments, the electronic address associated with the patient is obtained, without user intervention, from an electronic medical record associated with the patient, in response to receiving the prescription request. In some embodiments, the identification of the patient associated with the user includes the electronic address associated with the patient.

In some embodiments, the method further comprises storing an indication that the user has prescribed the first health care application in a user profile associated with the user.

In some embodiments, the method further comprises receiving a prescription history request from the user. There is obtained, from a user profile associated with the user, a second subset of health care applications in the plurality of health care applications, where the user has prescribed each respective heath care application in the second subset of heath care applications to one or more patients. This prescription history information, for the user for the second subset of health care applications, is communicated to the user. In some embodiments, what is communicated is, for each respective health care application in the second subset of health care applications, (i) an identity of each patient the respective health care application was prescribed to by the user, (ii) an indication for each respective patient whether the patient downloaded and used the respective health care application, and (iii) a date the respective health care application was prescribed to the respective patient by the respective user. In some such embodiments, the prescription history information for the user is sortable by any one combination of (i) health care application name, (ii) patient name, (iii) prescription date, and (iv) whether or not the respective health care application has been downloaded by the patient.

In some embodiments, the method further comprises accessing a list of prescribed health care applications in a user profile associated with the user, where the user has prescribed each respective health care application in the list of prescribed health care applications to at least one patient, and each health care application in the set of prescribed health care applications that is also in the set of matching health care applications at the beginning of the sorted list of matching health care applications.

In some embodiments, the method further comprises receiving an information request from the user pertaining to an identified health care application in the search response and responsive to receiving the information request, providing (e.g., formatting for display) an information response, the information response including an application name for the identified health care application and a synopsis of the identified health care application.

In some embodiments, the user is not an author and is not associated with any health care application in the plurality of health care applications.

In some embodiments, a second health care application in the plurality of health care applications is ranked by individual members of a medical community thereby forming an overall ranking for the second health care application that is distinct from the evidence score for the second health care application. In some embodiments, the second health care application is included in the search query response along with the overall ranking.

In some embodiments, a curated subset of the plurality of health care applications is provided to the user for display prior to receiving a search query from the user. In some such embodiments, each respective health care application in the curated subset of health care applications is approved by a governing body (e.g., the United States Food and Drug Administration). In some such embodiments, each respective health care application in the curated subset of health care applications is approved by a sponsor, such as a research university, medical group, or hospital.

In some embodiments, a health care application in the set of matching health care applications is for a chronic gastrointestinal indication. In some embodiments, the chronic gastrointestinal indication is inflammatory bowel disease (e.g., Crohn's disease, ulcerative colitis, or indeterminate colitis), obesity, irritable bowel syndrome, gastrointestinal neoplasia, Celiac disease, a food allergy (e.g., to cow's milk, eggs, fish, peanuts, shell fish, soy, tree nuts, and/or wheat), or a food intolerance {e.g., to lactose, sucrose, maltose, histamine, tyramine, salicylate, tartrazine, benzoates, monosodium glutamate, and/or a food dye).

BRIEF DESCRIPTION OF THE DRAWINGS

FIGS. 5A, 5B, 5C, 5D, and 5E collectively provide a flow chart of processes and features of a system for providing a platform in which medical practitioners can search and browse for evidence-based digital medicine applications, rate them, and prescribe them to patients, in accordance with various embodiments of the present disclosure.

Like reference numerals refer to corresponding parts throughout the several views of the drawings.

DETAILED DESCRIPTION

Reference will now be made in detail to embodiments, examples of which are illustrated in the accompanying drawings. In the following detailed description, numerous specific details are set forth in order to provide a thorough understanding of the present disclosure. However, it will be apparent to one of ordinary skill in the art that the present disclosure may be practiced without these specific details. In other instances, well-known methods, procedures, components, circuits, and networks have not been described in detail so as not to unnecessarily obscure aspects of the embodiments.

It will also be understood that, although the terms first, second, etc. may be used herein to describe various elements, these elements should not be limited by these terms. These terms are only used to distinguish one element from another. For example, a first subject could be termed a second subject, and, similarly, a second subject could be termed a first subject, without departing from the scope of the present disclosure. The first subject and the second subject are both subjects, but they are not the same subject. Furthermore, the terms "subject" and "user" are used interchangeably herein.

The terminology used in the present disclosure is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

Figure 1:
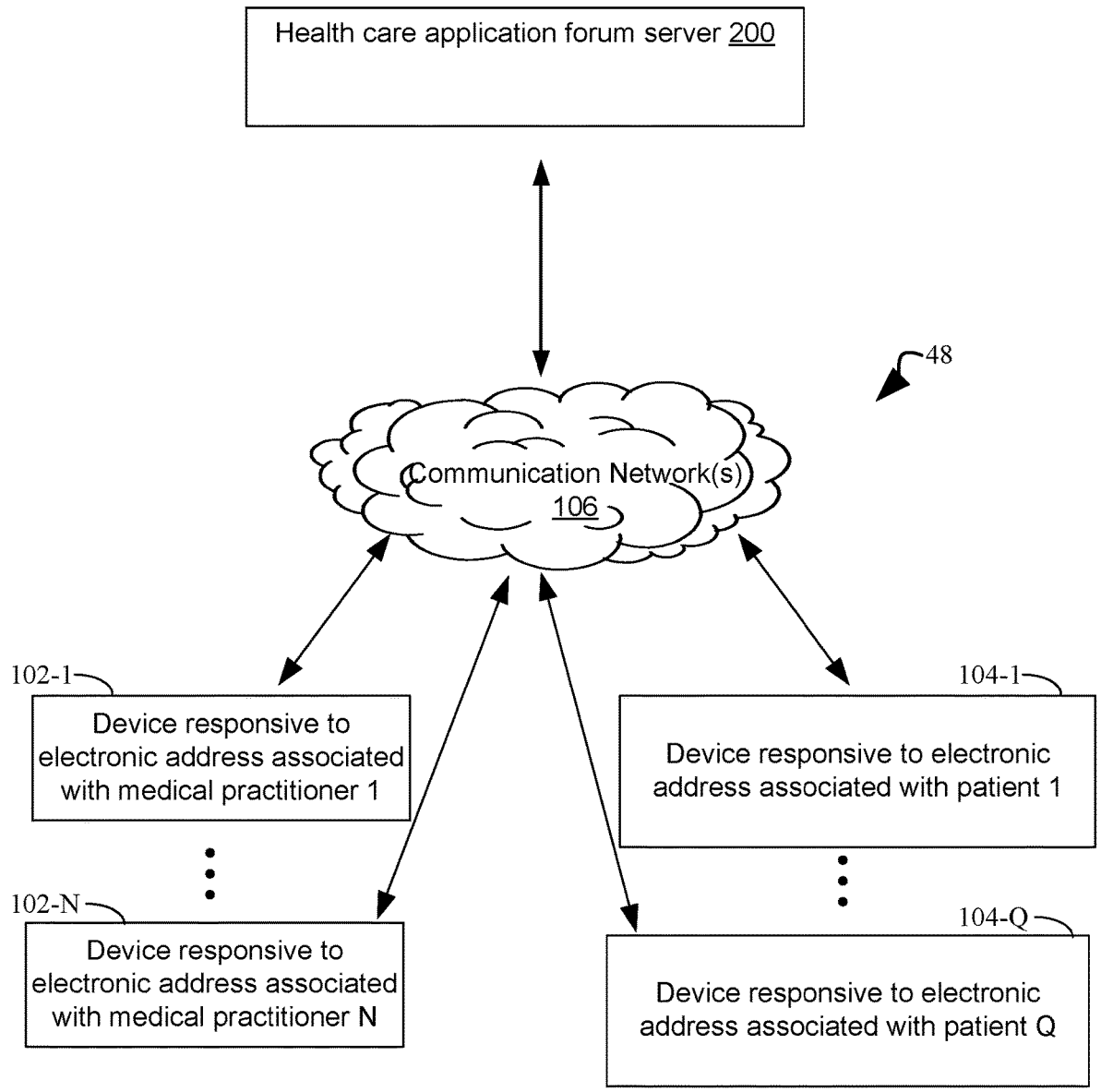
FIG. 1 illustrates a system topology in accordance with the present disclosure that includes a health care application forum server, a plurality of devices associated with medical practitioners that make use of the health care application forum server, and devices that are associated with patients that are prescribed health care applications from the health care application forum server by medical practitioners.
Figure 2:
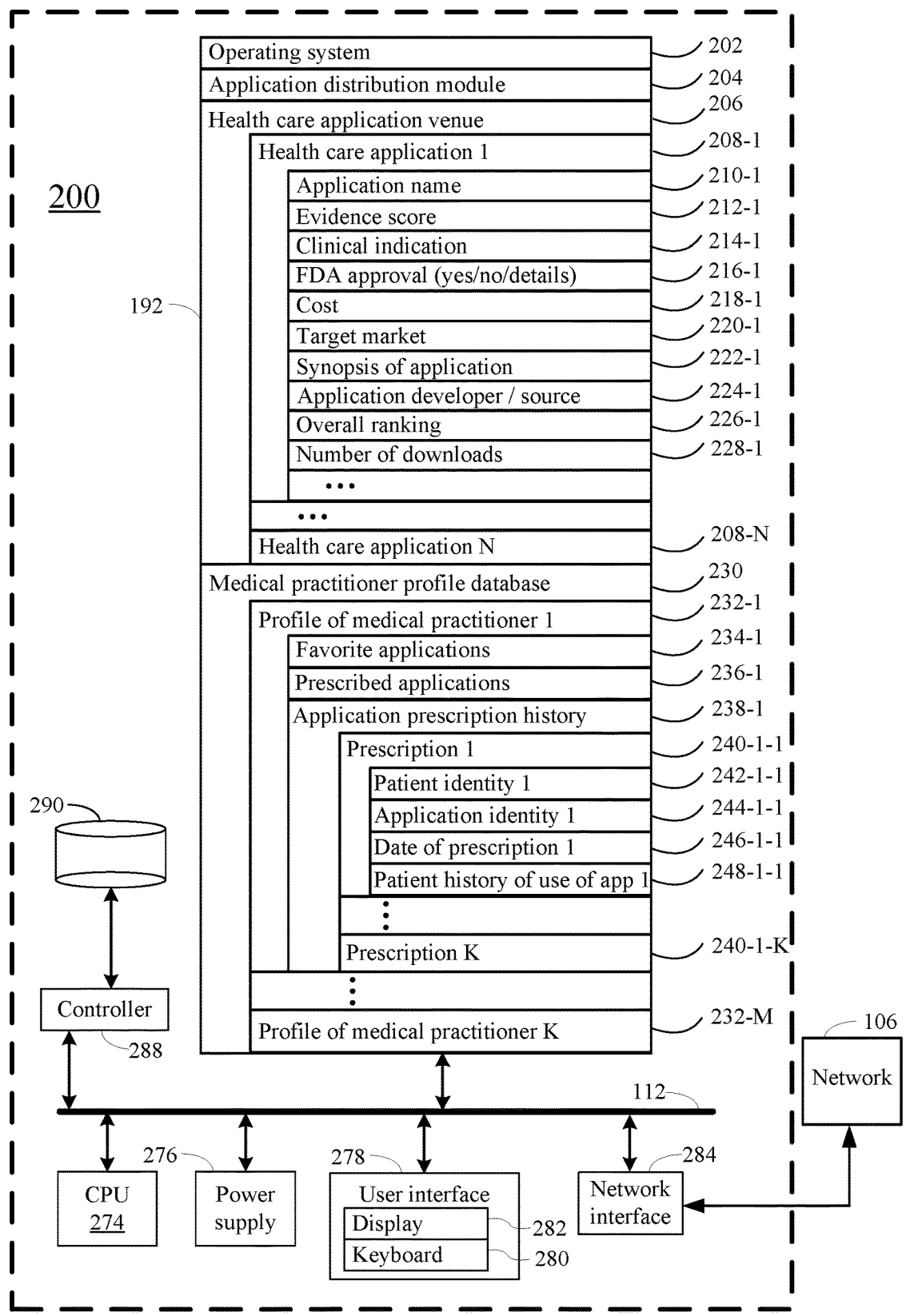
FIG. 2 illustrates a health care application forum server in accordance with an embodiment of the present disclosure.
Figure 3:
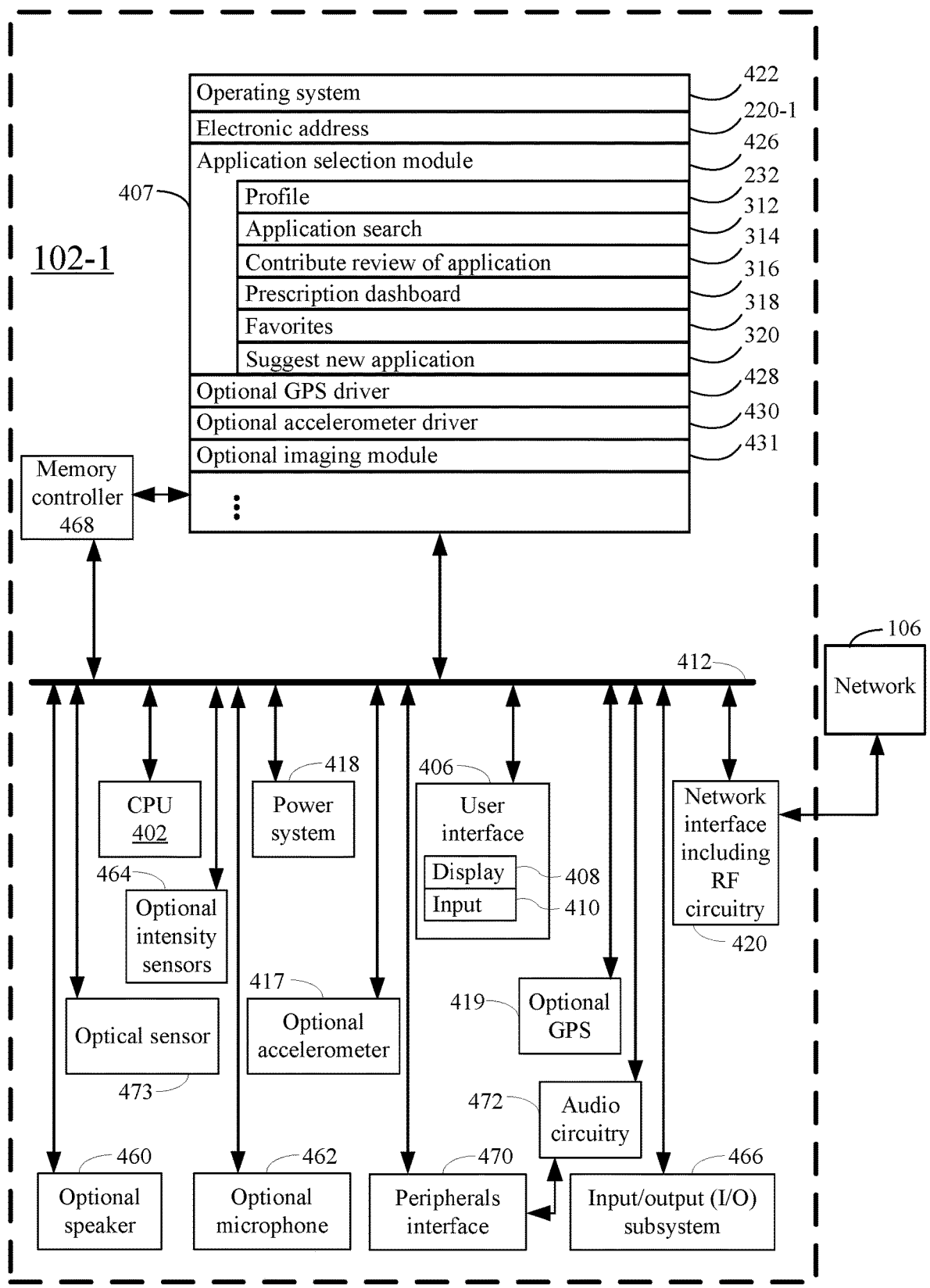
FIG. 3 illustrates a device associated with a medical practitioner, in accordance with an embodiment of the present disclosure.
Figure 4:
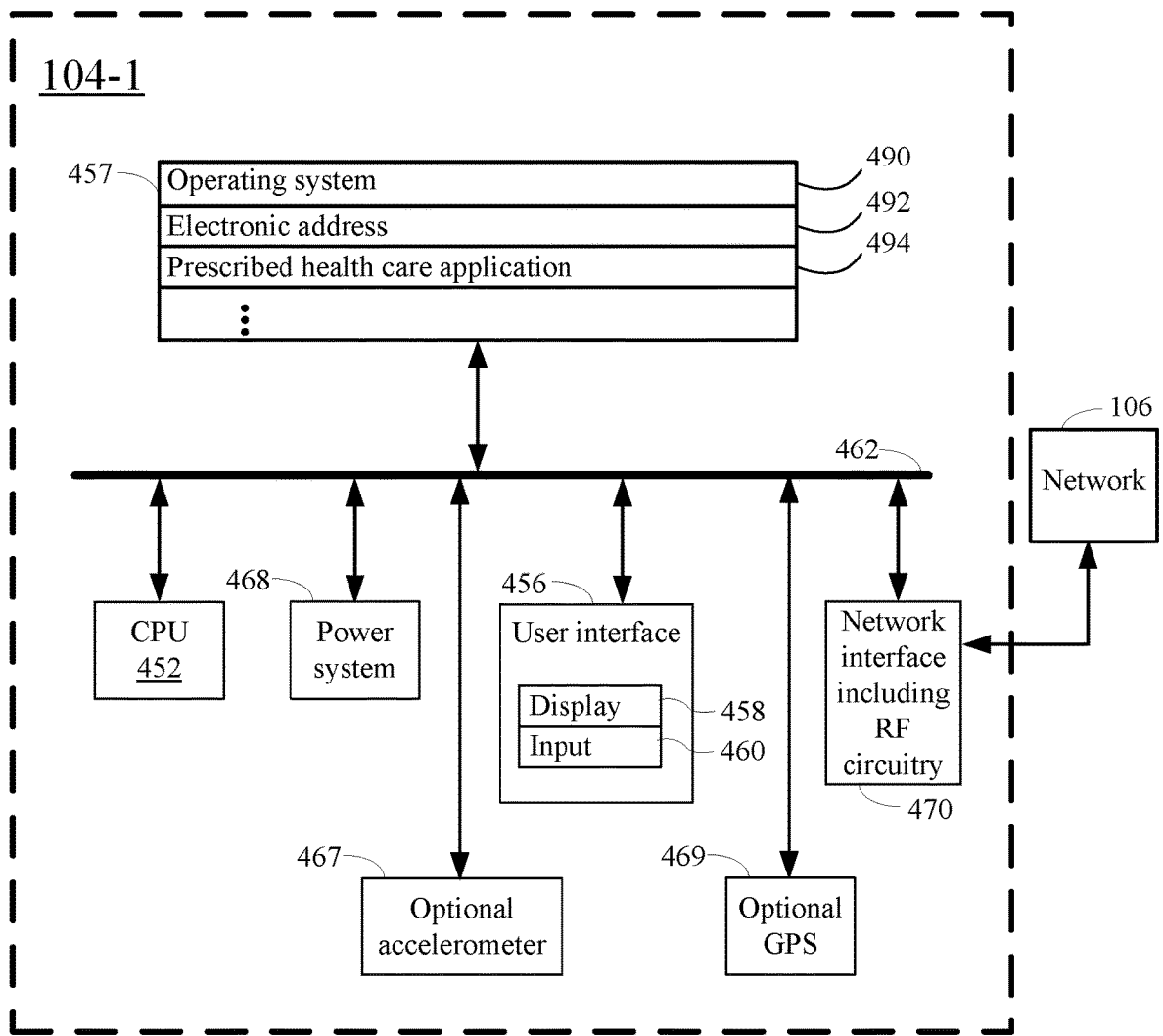
FIG. 4 illustrates a device associated with a patient, in accordance with an embodiment of the present disclosure.

A detailed description of a system 48 in which medical practitioners can search and browse for evidence-based digital medicine applications in accordance with the present disclosure is described in conjunction with FIGS. 1 through 4. As such, FIGS. 1 through 4 collectively illustrate the topology of the system in accordance with the present disclosure. In the topology, there is a health care application forum server 200 (FIGS. 1 and 2), devices 102 responsive to electronic addresses associated with medical practitioners (FIGS. 1 and 3), and devices 104 responsive to the electronic addresses associated with patients (FIGS. 1 and 4).

Of course, other topologies of system 48 are possible, for instance, health care application forum server 200 can in fact constitute several computers that are linked together in a network or be a virtual machine in a cloud computing context. As such, the exemplary topology shown in FIG. 1 merely serves to describe the features of an embodiment of the present disclosure in a manner that will be readily understood to one of skill in the art.

Referring to FIG. 2, in typical embodiments, a health care application forum server 200 comprises one or more computers. For purposes of illustration in FIG. 2, the health care application forum server 200 is represented as a single computer that includes all of the functionality of the health care application forum server 200. However, the disclosure is not so limited. The functionality of the health care application forum server 200 may be spread across any number of networked computers and/or reside on each of several networked computers and/or by hosted on one or more virtual machines at a remote location accessible across the communications network 106. One of skill in the art will appreciate that a wide array of different computer topologies are possible for the health care application forum server 200 and all such topologies are within the scope of the present disclosure.

Turning to FIG. 2 with the foregoing in mind, a health care application forum server 200 comprises one or more processing units (CPU's) 274, a network or other communications interface 284, a memory 192 (e.g., random access memory), one or more magnetic disk storage and/or persistent devices 290 optionally accessed by one or more controllers 288, one or more communication busses 112 for interconnecting the aforementioned components, and a power supply 276 for powering the aforementioned components. Data in memory 192 can be seamlessly shared with non-volatile memory 290 using known computing techniques such as caching. Memory 192 and/or memory 290 can include mass storage that is remotely located with respect to the central processing unit(s) 274. In other words, some data stored in memory 192 and/or memory 290 may in fact be hosted on computers that are external to the health care application forum server 200 but that can be electronically accessed by the health care application forum server over an Internet, intranet, or other form of network or electronic cable (illustrated as element 106 in FIG. 2) using network interface 284.

The memory 192 of health care application forum server 200 stores:
- an operating system 202 that includes procedures for handling various basic system services;
- an application distribution module 204 for distributing evidence-based digital medicine applications to a plurality of subjects;
- a health care application venue 206 that provides functionality for medical practitioners to search and browse for such applications, the health care application venue 206 tracking a plurality of health care applications (evidence-based digital medicine applications) 208, including for each such application the application name 210, an evidence score 212 that is generated by a plurality of health care providers and not end users, a clinical indication 214 for the application, whether or not the application has been approved by a regulatory body such as the United States Food and Drug Administration 216, a cost of the application 218, the target market for the application 220 (e.g., patients, medical practitioners, both patients and medical practitioners), a synopsis 222 of the application that provides a concise description of the application, the developer 224 of the application, an optional overall ranking 226 of the application, and optionally a number of times the application has been downloaded 228; and
- a medical practitioner profile database 230 that stores the medical profiles 232 of medical practitioners, such profiles including the favorite evidence-based digital medicine applications 234 and the prescribed evidence-based digital medicine applications 236 of the medical practitioners, as well as their application prescription histories 238 including, for each such prescription 240, which patient was prescribed 242, the identity of the evidence-based digital medicine application that was prescribed 244, the date of the prescription 246, and an indication of whether the patient makes use of the prescription 248.

In some embodiments, health care application venue 206 is a node.js web application built using AngularJS 1.4.3 framework hosted on an Azure back-end with a data model persisted in Microsoft SQL server and makes scheduled API calls to the iTunes store. Advantageously, in such embodiments, since it is a web application it is accessible on any browser (phone, tablet, laptop/desktop) such as device 102 of FIGS. 1 and 3. In some embodiments health care application venue 206 runs on native device frameworks, and is available for download onto devices 102 running operating systems such as Android and iOS.

In some implementations, one or more of the above identified data elements or modules of the health care application forum server 200 are stored in one or more of the previously described memory devices, and correspond to a set of instructions for performing a function described above. The above-identified data, modules or programs (e.g., sets of instructions) need not be implemented as separate software programs, procedures or modules, and thus various subsets of these modules may be combined or otherwise re-arranged in various implementations. In some implementations, the memory 192 and/or 290 optionally stores a subset of the modules and data structures identified above. Furthermore, in some embodiments the memory 192 and/or 206 stores additional modules and data structures not described above.

In some embodiments, a device 102 responsive to an electronic address of a medical practitioner is a smart phone (e.g., an iPHONE), laptop, tablet computer, desktop computer, or other form of electronic device (e.g., a gaming console). In some embodiments, a device 102 is not mobile. In some embodiments, a device 102 is mobile.

FIG. 3 provides a description of a device 102 that can be used with the instant disclosure. It has one or more processing units (CPU's) 402, peripherals interface 470, memory controller 468, a network or other communications interface 420, a memory 407 (e.g., random access memory), a user interface 406, the user interface 406 including a display 408 and input 410 (e.g., keyboard, keypad, touch screen), an optional accelerometer 417, an optional GPS 419, optional audio circuitry 472, an optional speaker 460, an optional microphone 462, one or more optional intensity sensors 464 for detecting intensity of contacts on the device 102 (e.g., a touch-sensitive surface such as a touch-sensitive display system 408 of the device 102), optional input/output (I/O) subsystem 466, one or more optional optical sensors 474, one or more communication busses 412 for interconnecting the aforementioned components, and a power system 418 for powering the aforementioned components.

In some embodiments, the input 410 is a touch-sensitive display, such as a touch-sensitive surface. In some embodiments, the user interface 406 includes one or more soft keyboard embodiments. The soft keyboard embodiments may include standard (QWERTY) and/or non-standard configurations of symbols on the displayed icons.

Device 102 optionally includes, in addition to accelerometer(s) 417, a magnetometer (not shown) and a GPS 419 (or GLONASS or other global navigation system) receiver for obtaining information concerning the location and orientation (e.g., portrait or landscape) of device 102.

It should be appreciated that device 102 is only one example of a multifunction device that may be used by medical practitioners when engaging with the health care application forum server 200, and that device 102 optionally has more or fewer components than shown, optionally combines two or more components, or optionally has a different configuration or arrangement of the components. The various components shown in FIG. 3 are implemented in hardware, software, firmware, or a combination thereof, including one or more signal processing and/or application specific integrated circuits.

Memory 407 optionally includes high-speed random access memory and optionally also includes non-volatile memory, such as one or more magnetic disk storage devices, flash memory devices, or other non-volatile solid-state memory devices. Access to memory 407 by other components of device 100, such as CPU(s) 407 is, optionally, controlled by memory controller 468.

Peripherals interface 470 can be used to couple input and output peripherals of the device to CPU(s) 402 and memory 407. The one or more processors 402 run or execute various software programs and/or sets of instructions stored in memory 407 to perform various functions for device 102 and to process data.

In some embodiments, peripherals interface 470, CPU(s) 402, and memory controller 468 are, optionally, implemented on a single chip. In some other embodiments, they are, optionally, implemented on separate chips.

RF (radio frequency) circuitry 108 of network interface 420 receives and sends RF signals, also called electromagnetic signals. RF circuitry 108 converts electrical signals to/from electromagnetic signals and communicates with communications networks and other communications devices via the electromagnetic signals. RF circuitry 420 optionally includes well-known circuitry for performing these functions, including but not limited to an antenna system, an RF transceiver, one or more amplifiers, a tuner, one or more oscillators, a digital signal processor, a CODEC chipset, a subscriber identity module (SIM) card, memory, and so forth. RF circuitry 108 optionally communicates with networks 106. In some embodiments, circuitry 108 does not include RF circuitry and, in fact, is connected to network 106 through one or more hard wires (e.g., an optical cable, a coaxial cable, or the like).

Examples of networks 106 include, but are not limited to, the World Wide Web (WWW), an intranet and/or a wireless network, such as a cellular telephone network, a wireless local area network (LAN) and/or a metropolitan area network (MAN), and other devices by wireless communication. The wireless communication optionally uses any of a plurality of communications standards, protocols and technologies, including but not limited to Global System for Mobile Communications (GSM), Enhanced Data GSM Environment (EDGE), high-speed downlink packet access (HSDPA), high-speed uplink packet access (HSDPA), Evolution, Data-Only (EV-DO), HSPA, HSPA+, Dual-Cell HSPA (DC-HSPDA), long term evolution (LTE), near field communication (NFC), wideband code division multiple access (W-CDMA), code division multiple access (CDMA), time division multiple access (TDMA), Bluetooth, Wireless Fidelity (Wi-Fi) (e.g., IEEE 802.11a, IEEE 802.11ac, IEEE 802.11ax, IEEE 802.11b, IEEE 802.11g and/or IEEE 802.11n), voice over Internet Protocol (VoIP), Wi-MAX, a protocol for e-mail (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), Instant Messaging and Presence Service (IMPS)), and/or Short Message Service (SMS), or any other suitable communication protocol, including communication protocols not yet developed as of the filing date of this document.

In some embodiments, audio circuitry 472, speaker 460, and microphone 462 provide an audio interface between a subject (medical practitioner) and device 102. The audio circuitry 472 receives audio data from peripherals interface 470, converts the audio data to an electrical signal, and transmits the electrical signal to speaker 460. Speaker 460 converts the electrical signal to human-audible sound waves. Audio circuitry 472 also receives electrical signals converted by microphone 462 from sound waves. Audio circuitry 472 converts the electrical signal to audio data and transmits the audio data to peripherals interface 470 for processing. Audio data is, optionally, retrieved from and/or transmitted to memory 407 and/or RF circuitry 420 by peripherals interface 470.

In some embodiments, power system 418 optionally includes a power management system, one or more power sources (e.g., battery, alternating current (AC)), a recharging system, a power failure detection circuit, a power converter or inverter, a power status indicator (e.g., a light-emitting diode (LED)) and any other components associated with the generation, management and distribution of power in portable devices.

In some embodiments, the device 102 optionally also includes one or more optical sensors 473. Optical sensor(s) 473 optionally include charge-coupled device (CCD) or complementary metal-oxide semiconductor (CMOS) phototransistors. Optical sensor(s) 473 receive light from the environment, projected through one or more lens, and converts the light to data representing an image. In conjunction with imaging module 431 (also called a camera module), optical sensor(s) 473 optionally capture still images and/or video. In some embodiments, an optical sensor is located on the back of device 102, opposite display system 408 on the front of the device, so that the touch screen is enabled for use as a viewfinder for still and/or video image acquisition. In some embodiments, another optical sensor 473 is located on the front of the device 102 so that the subject's image is obtained (e.g., to verify the health or condition of the subject, or to help diagnose a subject's condition remotely, etc.).

As illustrated in FIG. 3, a device 102 preferably comprises an operating system 422 that includes procedures for handling various basic system services. Operating system 422 (e.g., iOS, DARWIN, RTXC, LINUX, UNIX, OS X, WINDOWS, or an embedded operating system such as VxWorks) includes various software components and/or drivers for controlling and managing general system tasks (e.g., memory management, storage device control, power management, etc.) and facilitates communication between various hardware and software components.

A device 102 further comprises an electronic address 220 (a mobile phone number, social media account, or e-mail address) associated with the corresponding medical practitioner that is used in some embodiments by the health care application forum server 200 to communicate with the medical practitioner.

Figure 6:
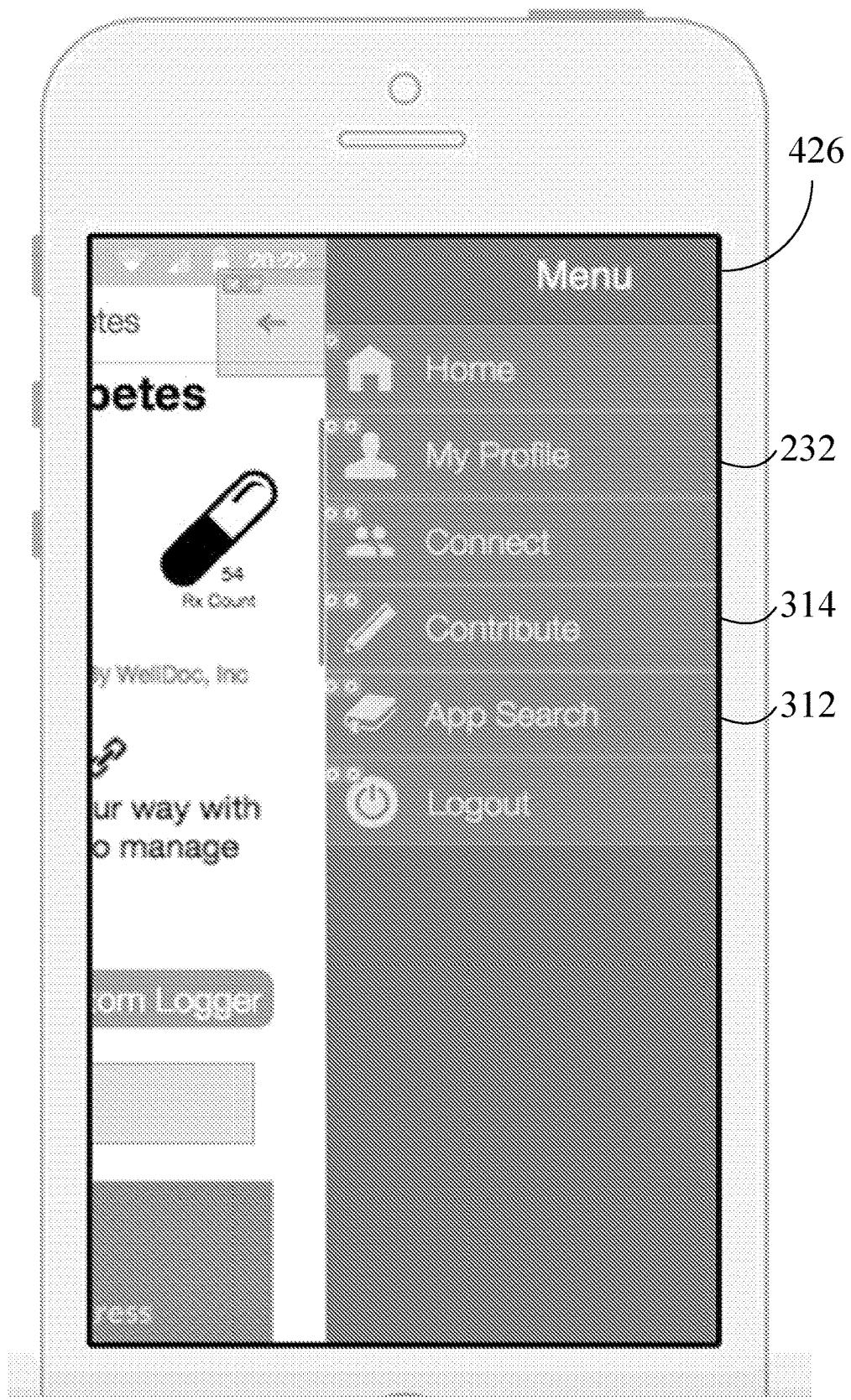
FIG. 6 illustrates an application selection module 426 in accordance with an embodiment of the present disclosure.

The device 102 further comprises an application selection module 426. FIG. 6 illustrates an application selection module 426 in accordance with an embodiment of the present disclosure. In some embodiments, the application selection module 426 is a node.js web application built using AngularJS 1.4.3 framework and the health care application venue 206 is an Azure back-end with a data model persisted in Microsoft SQL server that makes API calls to the iTunes store. Advantageously, in such embodiments, since the application selection module 426 is a web application it is accessible on any browser (phone, tablet, laptop/desktop) such as device 102 of FIGS. 1 and 3. In some embodiments application selection module 426 runs on native device frameworks, and is available for download onto devices 102 running operating systems 422 such as Android and iOS.

In some embodiments, the application selection module 426 provides a user profile 232 for the medical practitioner associated with the device 102, a module for searching for evidence-based digital medicine applications 312, an ability for the medical practitioner to contribute a review of a particular evidence-based digital medicine application 314, a prescription dashboard 316 which allows for the medical practitioner to see which applications the practitioner has prescribed, which patients have been prescribed these application, when they were prescribed, and whether the patients have used the applications. The application selection module 426 further allows the practitioner to designate particular applications that the practitioner likes as favorites 318. In some embodiments the practitioner's favorite applications are stores in the profile 232 of the user. In some embodiments, the application suggestion module 426 affords the practitioner the ability to suggest new evidence-based digital medicine applications to be included in the health care application venue 206 through the suggest new application 320 interface.

Referring to FIG. 4, in some embodiments a device 104 associated with a subject 216, is a smart phone. In other embodiments, a device 104 is not a smart phone but rather is a tablet computer, desktop computer, emergency vehicle computer, or other form of wired or wireless networked device. In some embodiments, device 104 has any or all of the circuitry, hardware components, and software components found in the device 102 depicted in FIG. 3. In the interest of brevity and clarity, only a few of the possible components of device 104 are shown in order to better emphasize the additional software modules that are installed on device 104.

In typical embodiments, device 104 has one or more processing units (CPU's) 452, a network or other communications interface 470, a memory 457 (e.g., random access memory), a user interface 456, the user interface 456 including a display 458 and input 460 (e.g., keyboard, keypad, touch screen), an optional accelerometer 467, an optional GPS 469, one or more communication busses 462 for interconnecting the aforementioned components, and a power system 468 for powering the aforementioned components. In some embodiments, the input 460 is touch-sensitive display, such as a touch-sensitive surface. In some embodiments, the user interface 456 may include one or more soft keyboard embodiments. The soft keyboard embodiments may include standard (QWERTY) and/or non-standard configurations of symbols on the displayed icons.

It should be appreciated that device 104 is only one example of a portable multifunction device, and that device 104 optionally has more or fewer components than shown in FIG. 4 (or in FIG. 3), optionally combines two or more components, or optionally has a different configuration or arrangement of the components. The various components shown in FIG. 4 are implemented in hardware, software, firmware, or a combination thereof, including one or more signal processing and/or application specific integrated circuits.

As illustrated in FIG. 4, a device 104 preferably comprises an operating system 490 that includes procedures for handling various basic system services. A device 104 further comprises an electronic address 492 (e.g., a mobile phone number, social media account, or e-mail address) associated with the caretaker that is used by the health care application forum server 200 to provide information, such as subscription notifications and/or evidence-based digital medicine applications 494 associated with such subscriptions.

In some embodiments, prescribed evidence-based digital medicine applications 494 allow for obtaining of data captured automatically at device 104 (e.g., activity, sleep cycle, etc.). In some such embodiments, a prescribed evidence-based digital medicine application 494 interfaces with other applications on the device 102 that collect such information. In some such embodiments, the prescribed evidence-based digital medicine application 494 interfaces (e.g., by a wireless connection, such as Bluetooth, or by wire) with devices worn by the subject (e.g., wearable biometric devices) that collect such information. Examples of such wearable devices include, but are not limited to, JAWBONE, MISFIT, FITBIT, GARMIN, MICROSOFT BAND 2, MOOV NOW and equivalents, XIAOMI MI BAND and equivalents, SWAROVSKI SHINE and equivalents. Non-limiting examples of such information that is collected by some (but not all) prescribed evidence-based digital medicine applications 494 in such embodiments are heart rate, sleep monitoring, daily step tracking, glucose detection, electroencephalograms, electrocaridograms, and electromyography.

In some instances, such data (e.g., from wearables, etc.) can come back from the application or related wearables and can be displayed back to the provider team or forwarded to an electronic medical record.

While the platform system 48 can work standalone, in some embodiments it can also be linked with electronic medical records to exchange information in any way.

In addition to health care applications, in some embodiments there are instances in which system 48 is used to find, rank or prescribe any actionable information including health education content, patient survey, care plans, devices or wearables or even teams of people to follow patients. Similarly, data can come back from patient surveys or devices etc. As such, in some embodiments, rather than health care applications, a set of health education content, patient survey, care plans, devices or wearables is individually assigned evidence scores and hosted by health care application forum server 200 in the same way that health care applications are offered. In some embodiments, each health care application 200 is a software program that is intended for use on a client device associated with a patient. In some embodiments, each health care application 200 is a software program.

Now that details of a system 48 in which medical practitioners can search and browse for evidence-based digital medicine applications has been disclosed, details regarding a flow chart of processes and features of the system, in accordance with an embodiment of the present disclosure, are disclosed with reference to FIGS. 5A through 5E.

Figure 7:
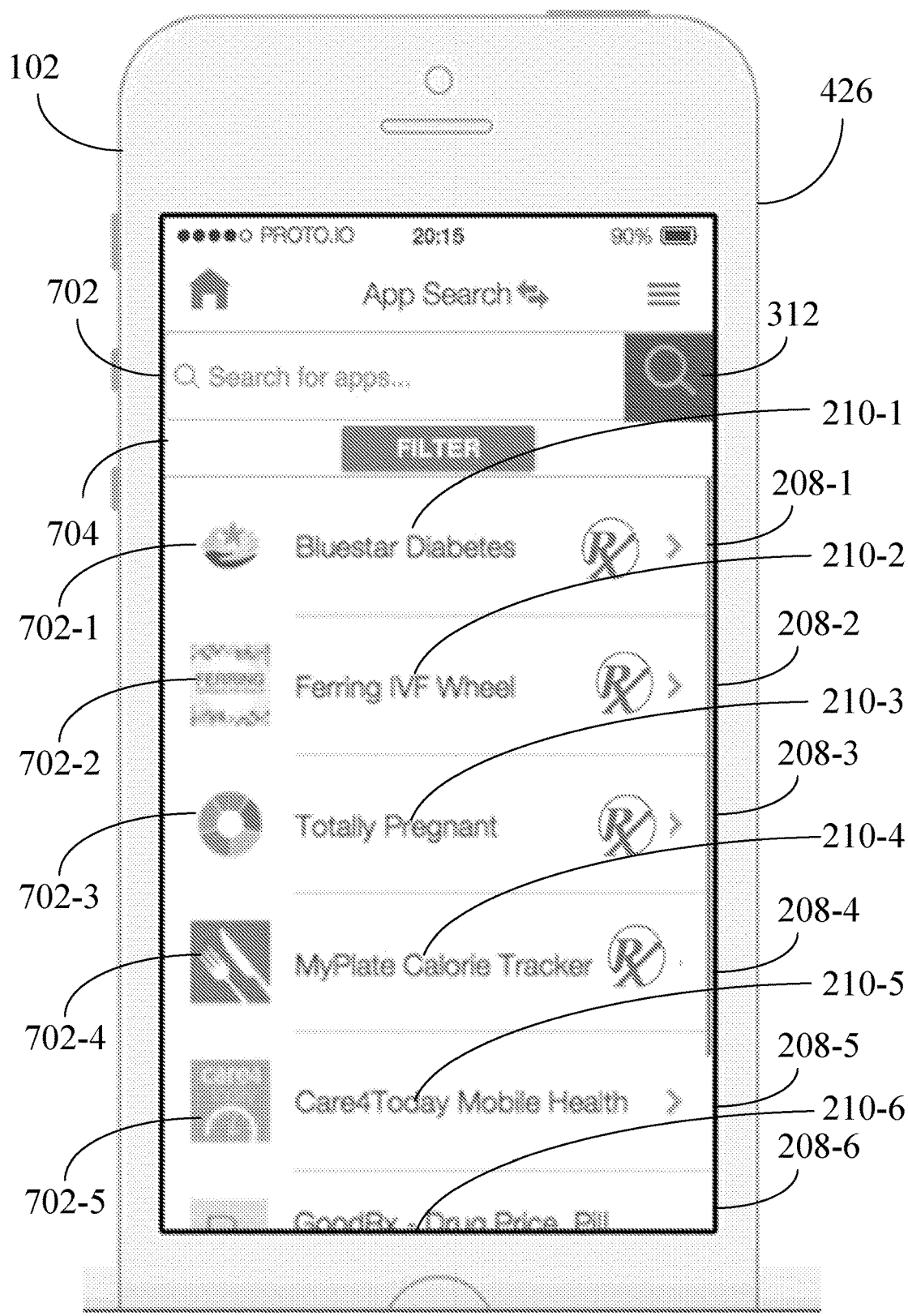
FIG. 7 illustrates how a user may enter an alphanumeric query at a prompt and enter a set of filtering criteria in order to perform a search for health care applications in accordance with an embodiment of the present disclosure.

Block 502. One aspect of the present disclosure provides a method which operates at a computer system, such as health care application forum server 200, and has one or more processors and memory storing one or more programs to be executed by the one of more processors to perform the method. In the method one or more health care applications are identified. A search request is received from a user at a remote client device (such as is a tablet or a smart phone (513)). For instance, a medical practitioner using the application search 312 feature of the application selection module 426 operating on device 102 (FIG. 3) may formulate a search request. In some embodiments the search request comprises an alphanumeric query and a set of filtering criteria. FIG. 7 illustrates. In FIG. 7, the user enters an alphanumeric query at prompt 702. For instance, if the medical practitioner is interested in health care applications pertaining to diabetes, the medical practitioner will enter the alphanumeric query "diabetes." Moreover, the medical practitioner may enter a set of filtering criteria using interface 704.

In some embodiments, the set of filtering criteria (i) includes an indication that the evidence score of each respective health care application in the set of matching health care applications is to exceed a minimum threshold value and (ii) provides a value for this minimum threshold value (504). For instance, in some embodiments the evidence score is on a scale of 0 to 5, where 0 indicates the poorest quality of clinical evidence of application efficacy and 5 indicates the greatest quality of clinical evidence. The medical researcher may be focused on providing to patients only those health care applications that have the strongest medical efficacy. In such situations, the medical practitioner may dial up the minimum threshold value to 4, thereby requiring that all matching health care applications have an evidence score of 4 or greater. On the other hand, the medical researcher may be focused on providing to patients health care applications that satisfy some other criteria, such as costs, linkage to electronic health records, etc., and may provide a low minimum threshold value such 1, thereby only requiring that all matching health care applications have an evidence score of 1 or greater. In still other embodiments, the health care practitioner may impose a threshold value of zero, thereby effectively permitting any health care application to match the evidence score requirement. While the scale range of 0 to 5 has been given, other possible ranges are possible. Moreover, in some embodiments the score is not on a numerical scale but rather is on a qualitative scale {e.g., bad, poor, unsatisfactory, satisfactory, good, excellent}.

In some embodiments, the set of filtering criteria includes a requirement that each respective health care application in the set of matching health care applications is approved by a governing body (e.g., the United States Food and Drug Administration) (506). In some embodiments, this requirement is a binary toggle, either the application has been approved or has not been. In this way, the medical practitioner can search for only those applications that have been approved if desired.

In some embodiments, the set of filtering criteria includes a requirement that each respective health care application in the set of matching health care applications provides a direct link (e.g., is a two way direct link, a one way direct link, or a partial direct link) to an electronic health record system (508). This is useful in situations where the medical practitioner would like to prescribe applications that are complaint with electronic health record systems. An electronic health record (EHR) is a digital version of a patient's paper chart. EHRs are real-time, patient-centered records that make information available instantly and securely to authorized users. While an EHR does contain the medical and treatment histories of patients, an EHR system is built to go beyond standard clinical data collected in a provider's office and can be inclusive of a broader view of a patient's care. In some embodiments, an EHR contain a patient's medical history, diagnoses, medications, treatment plans, immunization dates, allergies, radiology images, and laboratory and test results, and allow access to evidence-based tools that providers can use to make decisions about a patient's care. Through HER, health information can be created and managed by authorized providers in a digital format capable of being shared with other providers across more than one health care organization. EHRs are built to share information with other health care providers and organizations—such as laboratories, specialists, medical imaging facilities, pharmacies, emergency facilities, and school and workplace clinics—so they contain information from all clinicians involved in a patient's care.

In some embodiments, the set of filtering criteria includes a requirement regarding a cost (e.g., free, freemium, paid, other) of each respective health care application in the set of matching health care applications (510).

In some embodiments, the set of filtering criteria includes a requirement regarding a characteristic of the intended end user of each respective health care application in the set of matching health care applications. For instance, in some embodiments, the medical practitioner may filter the applications to select only those in which the intended application user is a patient, only those in which the intended application user is a medical provider, those in which the intended application user is either patient or provider, or those in which the intended application user is a health care team (512).

In some embodiments, the user of the application selection module 426 is not an author and is not associated with any health care application in the plurality of health care applications (514) hosted by the health care application forum server 200. Rather, in typical embodiments, the user of application selection module 426 is a medical practitioner that is seeking applications to offer (prescribe) to patients in order to address clinical indications.

Figure 8A:
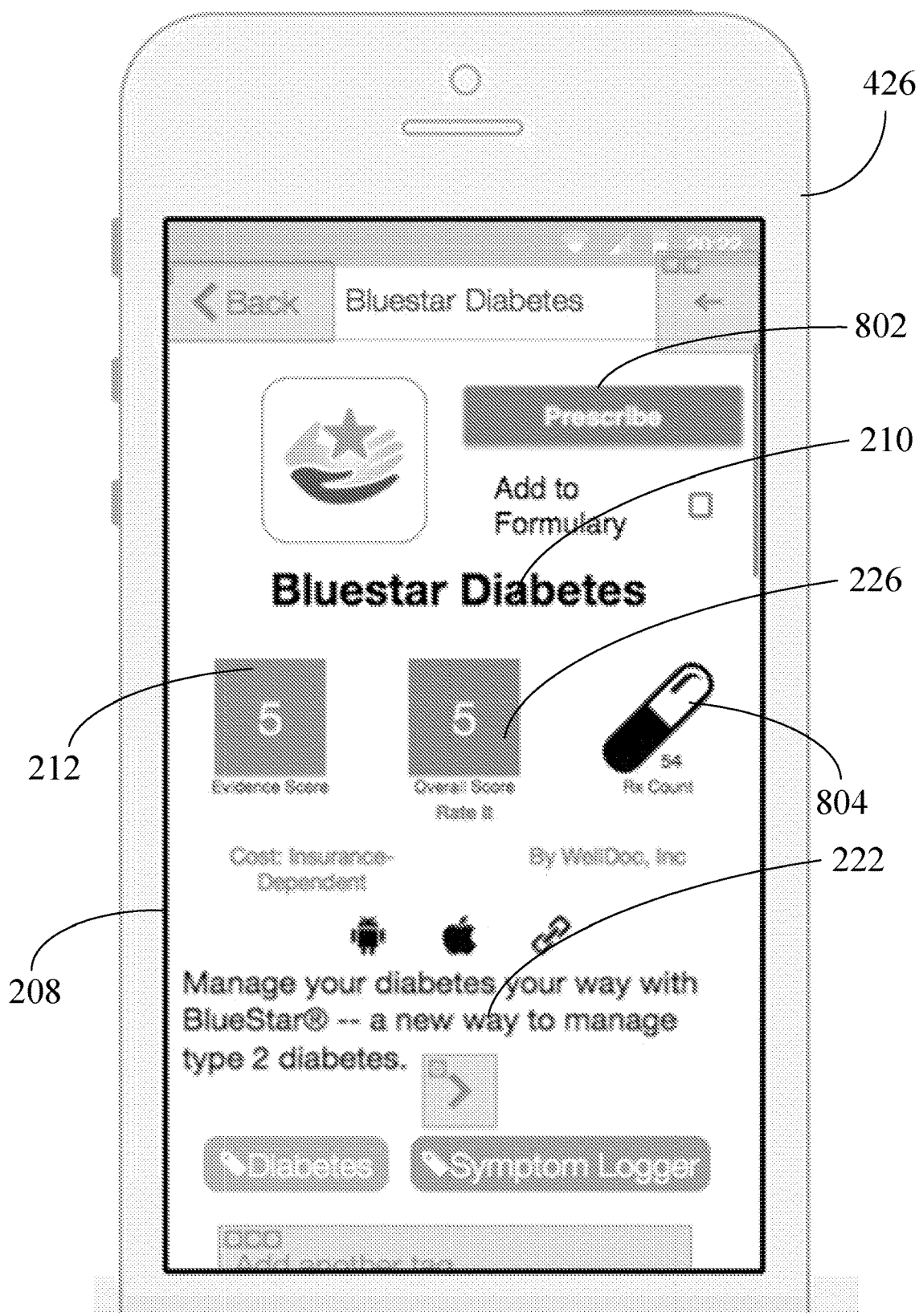
FIG. 8A illustrates an instance where the evidence score and the overall score (overall ranking) is displayed for a particular health care application within an application selection module in accordance with an embodiment of the present disclosure.
Figure 8B:
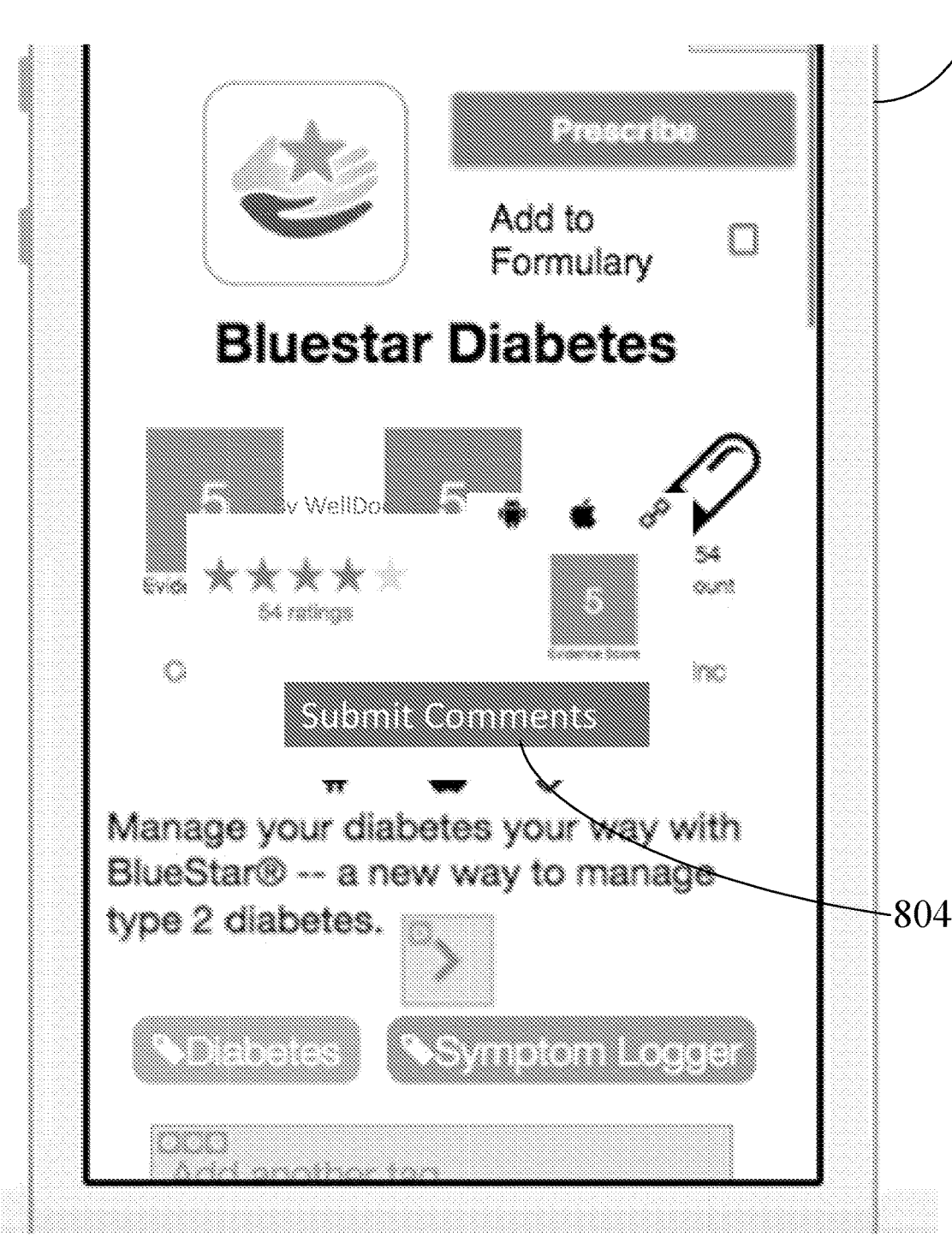
FIG. 8B how a medical practitioner may submit comments regarding a health care application in accordance with an embodiment of the present disclosure.
Figure 9:
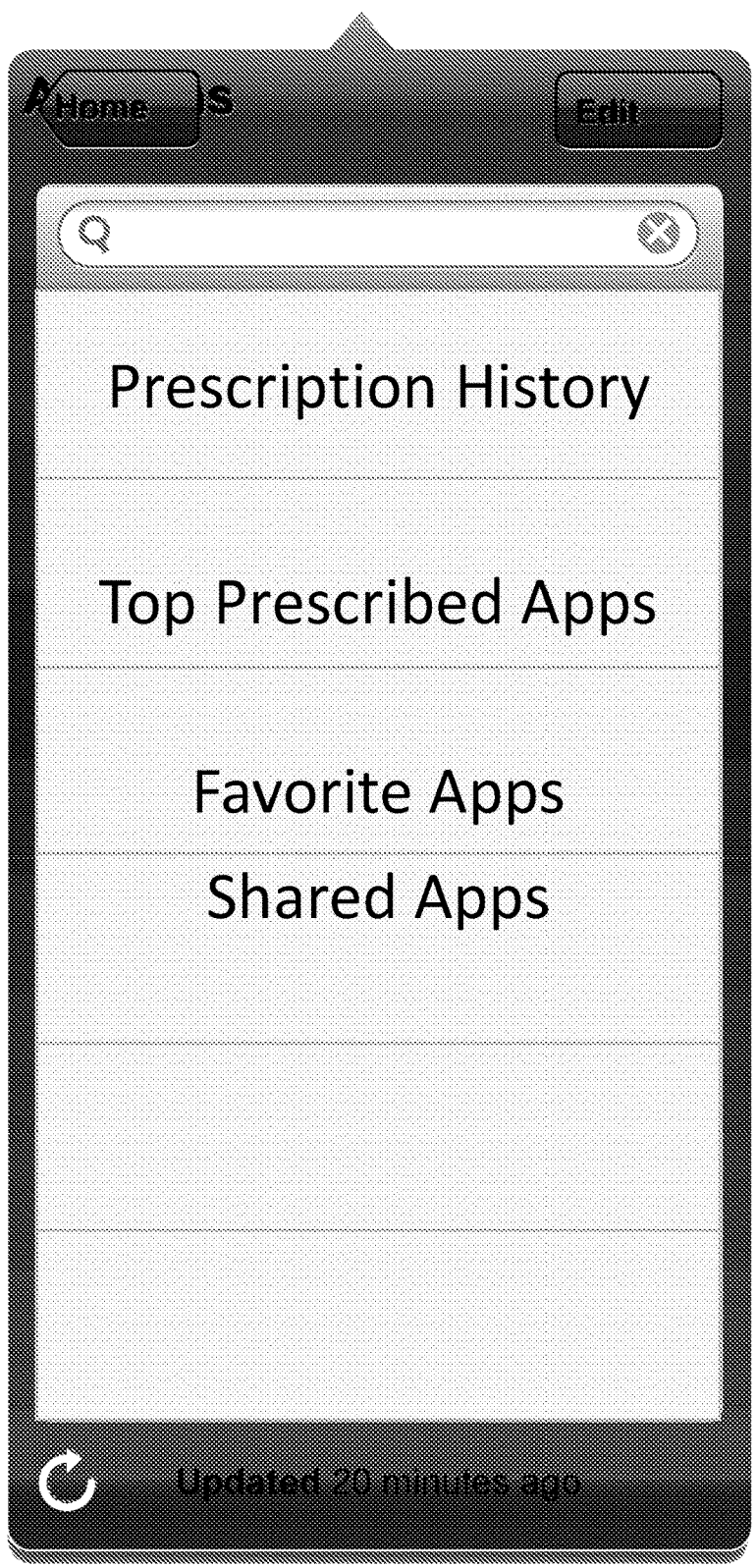
FIG. 9 illustrates an example profile 232 displayed to the user, including the user's prescription history, top prescribed applications, favorite applications, and shared applications in accordance with an embodiment of the present disclosure.

In some embodiments, the medical community has access to the clinical data for applications and rates the clinical efficacy of such applications on the basis of this clinical data in order to form the evidence score. In some embodiments medical practitioners rate the clinical data on a scale of 0 to 5, in which 0 means not rated, 1 means unsure evidence, 2 means efficacy in cross-sections or retrospective study, 3 means efficacy in prospective study, 4 means efficacy in randomized clinical trial, and 5 means efficacy in multiple trials in multiple settings. In some embodiments, the evidence score is an average of the score given by those members of the medical community that have rated the application using such a scale. In some embodiments, a special rating committee is formed from suitable members of the medical community to provide an evidence score to applications based on the clinical data for such applications. Separate and apart from this evidence score, in some embodiments 515, health care applications in the plurality of health care applications provided by the health care application forum server 200 are ranked by individual members of a medical community thereby forming an overall ranking for the second health care application (i.e., that is distinct from the evidence score). This ranking may be on criteria other than or in addition to the clinical evidence for such applications, such as the ease of use or reliability of the applications. In some embodiments, the evidence score 212 is established based on clinical evidence of efficacy by a medical committee and the overall score 226 is established by users of the system, such as medical practitioners. FIG. 8A illustrates an instance where the evidence score 212 and the overall score (overall ranking) 226 is displayed for a particular health care application 208 within the application selection module 426. FIG. 8B how a medical practitioner may submit comments regarding a health care application in accordance with an embodiment of the present disclosure. FIG. 9 illustrates an example profile 232 displayed to the user upon selection of the "My Profile" affordance of FIG. 6, including the user's prescription history, top prescribed applications, favorite applications, and shared applications. Here shared applications means applications that are shared with other medical practitioners, in contrast to being prescribed to patients.

Block 516. With the search query in hand, a plurality of health care applications is searched to identify health care applications in the plurality of health care applications that satisfy each filtering criterion in the set of filtering criteria and further match the alphanumeric query thereby identifying a set of matching health care applications. In some such embodiments, the search query entered by the medical practitioner through the application selection module 426 is communicated to the health care application venue 206 on server 200 in order to find the matching health care applications. Each respective health care application in the plurality of health care applications traced by the health care application venue is (i) for a clinical indication and (ii)

includes an evidence score that is generated by a plurality of health care providers and not end users.

In some embodiments, the clinical indication of a health care application in the set of matching health care applications is a chronic gastrointestinal indication (e.g., inflammatory bowel disease, obesity, irritable bowel syndrome, gastrointestinal neoplasia, Celiac disease, a food allergy, or a food intolerance) (517). In some such embodiments, the user designates this clinical indication in the alphanumeric search query (e.g., by specifying inflammatory bowel disease, obesity, irritable bowel syndrome, gastrointestinal neoplasia, Celiac disease, a food allergy, or a food intolerance).

In some embodiments, the clinical indication of a health care application in the set of matching health care applications is a disease (518). In some such embodiments, the user designates this clinical indication in the alphanumeric search query (e.g., by specifying a particular cancer).

In some embodiments, the clinical indication of a health care application in the set of matching health care applications is an allergy (520). In some such embodiments, the user designates this clinical indication in the alphanumeric search query (e.g., by specifying a particular type of allergy).

In some embodiments, the clinical indication of a health care application in the set of matching health care applications is a cancer (e.g., liver cancer, breast cancer, brain cancer, colon cancer, pancreatic cancer, lung cancer, stomach cancer, bone cancer, or a leukemia) (522). In some such embodiments, the user designates this clinical indication in the alphanumeric search query (e.g., by specifying a particular cancer).

In some embodiments, the clinical indication of a health care application in the set of matching health care applications is a disorder of the brain or nervous system (524). In some such embodiments, the user designates this clinical indication in the alphanumeric search query (e.g., by specifying a disorder of the brain or nervous system).

In some embodiments, the clinical indication of a health care application in the set of matching health care applications is an eye disorder, an ear disorder, or a heart disorder (526). In some such embodiments, the user designates this clinical indication in the alphanumeric search query (e.g., by specifying a particular eye disorder, ear disorder, or heart disorder).

In some embodiments, the clinical indication of a health care application in the set of matching health care applications is a heart or circulation disorder (528). In some such embodiments, the user designates this clinical indication in the alphanumeric search query (e.g., by specifying a particular heart or circulation disorder).

In some embodiments, the clinical indication of a health care application in the set of matching health care applications is a blood disorder, a disorder of the urinary tract, a hormonal disorder, a muscle disorder, a bone disorder, or a joint disorder (530). In some such embodiments, the user designates this clinical indication in the alphanumeric search query (e.g., by specifying a particular blood disorder, disorder of the urinary tract, hormonal disorder, muscle disorder, bone disorder, or joint disorder).

Block 534. Turning to FIG. 5C, a search query response is formatted for display by the health care application venue 206 upon completion of the search of the plurality of health care applications 208 for matches. The search query response includes an identification of each respective health care application in the set of matching health care applications. The formatting includes sorting the set of matching health care applications by sorting criteria thereby forming a sorted list of matching health care applications. At least a portion of the sorting criteria is the evidence score. For example, in some embodiments, the set of matching health care applications is rank ordered by their evidence scores, with those applications having better evidence scores ranked higher than those applications that have worse evidence scores.

In some embodiments the medical practitioner that made the search query has a list of favorite health care applications (e.g., stored as favorite applications 234 in the profile 232 of the medical practitioner in the medical practitioner profile database 230). In some such embodiments, this list of favorite health care applications is accessed in the user profile associated with the user. Each health care application in the set of matching health care applications that is also in the list of favorite health care applications is placed at the beginning of the sorted list of matching health care applications (536). For example, consider the case where the set of matching health care applications consist of four applications, application 1 (evidence score 3.5), application 2 (evidence score 3.0), application 3 (evidence score 2.5) and application 4 (evidence score 2.0) and application 4 is also designated as a favorite of the search requester. In this instance, application 4 will be listed before the other applications in the formatted search query response even though it has a lower evidence score because it has been designated as a favorite application of the search requester.

In some embodiments the medical practitioner that made the search query has a list of prescribed applications (e.g., stored as prescribed applications 236 in the profile 232 of the medical practitioner in the medical practitioner profile database 230). Such applications are the applications that the medical practitioner (user) has prescribed to patients. In some such embodiments, the list of prescribed health care applications is accessed in the user profile associated with the user. The user has prescribed each respective health care application in the list of prescribed health care applications to at least one patient. In such embodiments, the formatting of the search query results further comprises placing each health care application in the set of prescribed health care applications that is also in the set of matching health care applications at the beginning of the sorted list of matching health care applications (538). For example, consider the case where the set of matching health care applications again consist of four applications, application 1 (evidence score 3.5), application 2 (evidence score 3.0), application 3 (evidence score 2.5) and application 4 (evidence score 2.0) and application 2 is also designated as an application that the search requester (user, medical practitioner) has prescribed. In this instance, application 2 will be listed before the other applications in the formatted search query response even though it does not have the best evidence score because it has been designated as prescribed application of the search requester.

Block 540. Turning to block 540 of FIG. 5C, process control continues with the communication of the search query response, including the sorted list of matching health care applications, to the remote client device. In other words, health care application venue 206 on server 200 communicates the search query response to application selection module 426 on client device 102 where it is displayed. For instance, turning to FIG. 7, each application 208 in the sorted list of matching health care applications is displayed in a formatted list with identifying information such as a logo 702 and name 210.

In some embodiments, a favorite health care application request is received from the user at the remote client device (542). In such instances, there is obtained, from a user profile 232 associated with the user, a first subset of health care applications in the plurality of health care applications (e.g., favorite applications 234 of FIG. 2). The user has designated each respective heath care application in the first subset of heath care applications as a favorite health care application. This first subset of health care applications is communicated to the remote client device (540) so that the user may review the user's favorite applications.

In some embodiments, a prescription request is received from the user at the remote client device. The prescription request comprises (i) an identification of a first health care application in the sorted list of matching health care applications from the user at the remote client device and (ii) an identification of the patient associated with the user. For instance, turning to FIG. 8A, while reviewing the health care application 208, the user may decide to prescribe the application to a patient by hitting the "prescribe" affordance 802. Responsive to receiving the identification, an invitation is sent to use the first health care application to an electronic address associated with the patient (544). In some embodiments, the electronic address associated with the patient is obtained, without user intervention, from an electronic medical record associated with the patient, in response to receiving the prescription request (546). In some embodiments, the identification of the patient associated with the user includes the electronic address associated with the patient (548). In some embodiments, an indication that the user has prescribed the first health care application to a patient is stored in the user profile 232 associated with the user (550).

Figure 10:
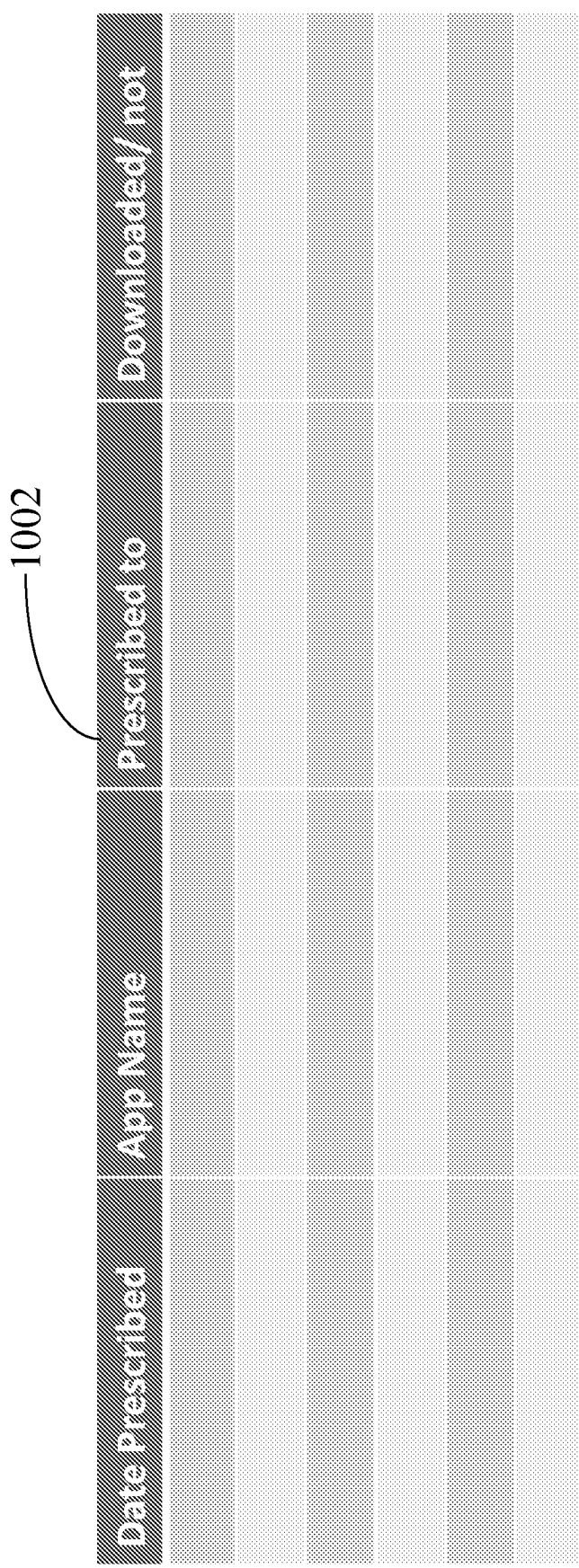
FIG. 10 illustrates a table that may be populated with such prescription information in accordance with some embodiments.

In some embodiments, a prescription history request is received from the user at the remote client device 102. In response to this request, there is obtained, from the user profile 232 associated with the user, an identification of those health care applications 236 in the plurality of health care applications that the user has prescribed. The user has prescribed each respective heath care application in the second subset of heath care applications to one or more patients. In some embodiments this user profile 232 is stored on server 200 as illustrated in FIG. 2. However, in some alternative embodiments, this user profile 232 is stored in a virtual machine in a cloud based computing environment. In still other embodiments, this user profile 232 is stored on the device 102 associated with the user. In embodiments where the user profile is stored in the health care application forum server, the prescription history information for the user is communicated from the health care application forum server 200 to the remote client device (554). In some such embodiments, for each respective health care application in the set of health care applications that user has subscribe, what is provided is (i) an identity of each patient the respective health care application was prescribed to by the user, (ii) an indication for each respective patient whether the patient downloaded and used the respective health care application, and (iii) a date the respective health care application was prescribed to the respective patient by the respective user (554). FIG. 10 illustrates a table 1002 that may be populated with such prescription information in accordance with some embodiments. In some embodiments, the prescription history information for the user is sortable by any one combination of (i) health care application name, (ii) patient name, (iii) prescription date, and (iv) whether or not the respective health care application has been downloaded by the patient (556).

Figure 5E:
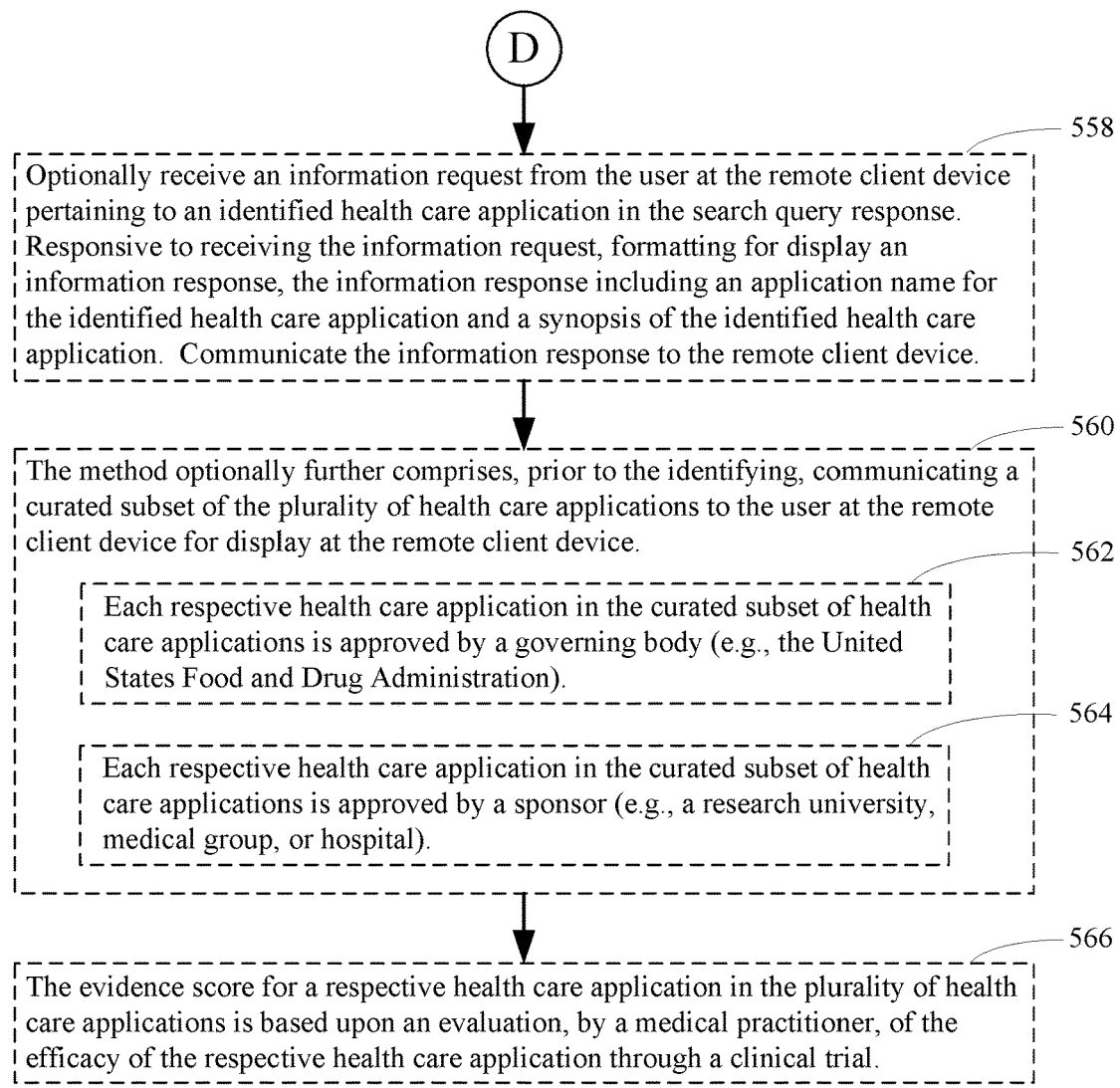

Referring to block 558 of FIG. 5E, in some embodiments an information request from the user at the remote client device 102 pertaining to an identified health care application in the search query response is received in some optional embodiments. For instance, in some embodiments, this form of user request may be on a particular application 208 in the formatted list of user applications returned from a search query. To illustrate in FIG. 7, a user may tap on the "Bluestar Diabetes" application 208 in order to form an information request pertaining to this application. Responsive to this information request, more information regarding the application is displayed in FIG. 8A, including the evidence score rating 212, the overall score 226, and the title of the application 210. A number of times the user has prescribed the application (prescription count 804) is also displayed in this additional information. A brief synopsis 222 of the application is also displayed in this additional information. Thus, in some embodiments, responsive to receiving the information request, an information response is formatted for display. In some embodiments, the information response includes an application name 210 for the identified health care application and a synopsis of the identified health care application 222. This information response is communicated to the remote client device (558).

In some embodiments, the method optionally further comprises, prior to receiving any search query from the user, communicating a curated subset of the plurality of health care applications to the user at the remote client device 102 for display at the remote client device (560). For instance, in some embodiments, turning to FIG. 7, the list of applications 208 shown is a pre-populated list of applications not responsive to any query provided by the user. In typical implementations, when the user provides the above-described search query, the search query results replace this pre-populated list. The pre-populated list constitutes a curated subset of health care application available from the health care application venue 206. In some embodiments, each respective health care application in the curated subset of health care applications is approved by a governing body (e.g., the United States Food and Drug Administration) (562). In some embodiments, each respective health care application in the curated subset of health care applications is approved by a sponsor (e.g., a research university, medical group, or hospital) (564).

In some embodiments, the evidence score for a respective health care application in the plurality of health care applications is based upon an evaluation, by a medical practitioner, of the efficacy of the respective health care application through a clinical trial (566).

REFERENCES CITED AND ALTERNATIVE EMBODIMENTS

All references cited herein are incorporated herein by reference in their entirety and for all purposes to the same extent as if each individual publication or patent or patent application was specifically and individually indicated to be incorporated by reference in its entirety for all purposes.

The present invention can be implemented as a computer program product that comprises a computer program mechanism embedded in a nontransitory computer readable storage medium. For instance, the computer program product could contain the program modules shown in any combination of FIG. 1, 2, 3, or 4. These program modules can be stored on a CD-ROM, DVD, magnetic disk storage product, or any other non-transitory computer readable data or program storage product.

Many modifications and variations of this invention can be made without departing from its spirit and scope, as will be apparent to those skilled in the art. The specific embodiments described herein are offered by way of example only. The embodiments were chosen and described in order to best explain the principles of the invention and its practical applications, to thereby enable others skilled in the art to best utilize the invention and various embodiments with various modifications as are suited to the particular use contemplated. The invention is to be limited only by the terms of the appended claims, along with the full scope of equivalents to which such claims are entitled.

What is claimed is:

1. A method comprising:
at a computer system having one or more processors and memory storing one or more programs to be executed by the one of more processors to perform the method, for each respective user in a plurality of users:
displaying, at a remote client device associated with the respective user, an application distribution module (204) comprising a plurality of health care applications, wherein each respective health care application in the plurality of health care applications is (i) for a clinical indication and (ii) includes an evidence score that is generated by a plurality of health care providers and not end users;
accessing, from a user profile database (230) stored in electronic form, a respective user profile (232) associated with the respective user, the user profile comprising:
(i) a set of favorite health care applications (234) for the respective user, selected from the plurality of health care applications,
(ii) a set of prescribed health care applications (236) selected from the plurality of health care applications, wherein each respective prescribed health care application in the set of prescribed health care applications has been prescribed, by the user, to a respective one or more patients in a plurality of patients associated with the user, and
(iii) for each respective prescribed health care application in the set of prescribed health care applications, an application prescription history (238) comprising an identity of each patient in the respective one or more patients to which the respective health care application has been prescribed;
receiving a search request from the respective user at the remote client device, wherein the search request comprises an alphanumeric query and a set of filtering criteria;
searching, at a health care application venue (206) that tracks the plurality of health care applications, the plurality of health care applications to identify one or more health care applications in the plurality of health care applications that (i) satisfy each respective filtering criterion in the set of filtering criteria and (ii) match the alphanumeric query, thereby identifying a set of matching health care applications, wherein the set of filtering criteria (i) includes an indication that the evidence score of each respective health care application in the set of matching health care applications is to exceed a minimum threshold value and (ii) provides a value for this minimum threshold value;
formatting for display a search query response, wherein the search query response includes an identification of each respective health care application in the set of matching health care applications, and wherein the formatting includes (i) sorting the set of matching health care applications by a plurality of sorting criteria thereby forming a sorted list of matching health care applications, wherein at least a portion of the sorting criteria is based upon the evidence score of each respective health care application in the set of matching health care applications, and (ii) placing each health care application in the set of matching health care applications that is also in the set of prescribed health care applications at the beginning of the sorted list of matching health care applications;
communicating the search query response including the sorted list of matching health care applications to the remote client device for display,
receiving a prescription request from the respective user at the remote client device via user selection of an affordance in the search query response, the prescription request comprising (i) an identification of a first health care application in the sorted list of matching health care applications from the respective user at the remote client device and (ii) an identification of a first patient in the plurality of patients associated with the respective user;
responsive to receiving the prescription request, sending an invitation to use the first health care application to an electronic address associated with the first patient, thereby prescribing the first health care application to the first patient; and
responsive to receiving a prescription history request from the respective user at the remote client device:
obtaining the set of prescribed health care applications from the respective user profile associated with the respective user; and
communicating the set of prescribed health care applications to the remote client device for display, wherein each respective prescribed health care application in the displayed set of prescribed health care applications is sortable by at least an indication, for each respective patient in the respective one or more patients, that the respective health care application was downloaded by the patient.

2. The method of claim 1, wherein the set of filtering criteria includes a requirement that each respective health care application in the set of matching health care applications provides a direct link to an electronic health record system.

3. The method of claim 1, wherein the set of filtering criteria includes a requirement regarding a cost of each respective health care application in the set of matching health care applications.

4. The method of claim 1, wherein the set of filtering criteria includes a requirement regarding a characteristic of the intended end user of each respective health care application in the set of matching health care applications, and wherein the characteristic is (a) patient, (b) provider, (c) patient or provider, or (d) health care team.

5. The method of claim 1, the method further comprising:
accessing the set of favorite health care applications in the user profile associated with the respective user and wherein the formatting further comprises placing each health care application in the set of matching health care applications that is also in the set of favorite health care applications at the beginning of the sorted list of matching health care applications.

6. The method of claim 1, the method further comprising:
receiving a favorite health care application request from the user at the remote client device;
obtaining the set of favorite health care applications from the user profile associated with the respective user, wherein the user has designated each respective heath care application in the set of favorite heath care applications as a favorite health care application; and
communicating the set of favorite health care applications to the remote client device.

7. The method of claim 1, the method further comprising communicating to the remote client device, for each respective health care application in the set of prescribed health care applications, (i) an identity of each patient the respective health care application was prescribed to by the respective user, (ii) an indication for each respective patient whether the patient downloaded and used the respective health care application, and (iii) a date the respective health care application was prescribed to the respective patient by the respective user wherein the prescription history information for the user is sortable by any one combination of (i) health care application name, (ii) patient name, (iii) prescription date, and (iv) whether or not the respective health care application has been downloaded by the patient.

8. The method of claim 1, the method further comprising:
receiving an information request from the user at the remote client device pertaining to an identified health care application in the search query response; and
responsive to receiving the information request, formatting for display an information response, the information response including an application name for the identified health care application and a synopsis of the identified health care application; and
communicating the information response to the remote client device.

9. The method of claim 1, wherein each respective health care application in the plurality of health care applications further includes an overall ranking that is (i) generated by a plurality of health care providers, (ii) distinct from the evidence score for the respective health care application, and (iii) based on at least one criterion that is not used to generate the evidence score for the respective health care application, and wherein the search query response further includes the overall ranking for each respective health care application in the set of matching health care applications.

10. The method of claim 1, wherein the clinical indication of a health care application in the set of matching health care applications is a chronic gastrointestinal indication.

11. The method of claim 10, wherein the chronic gastrointestinal indication is inflammatory bowel disease, obesity, irritable bowel syndrome, gastrointestinal neoplasia, Celiac disease, a food allergy, or a food intolerance.

12. The method of claim 1, wherein the clinical indication of a health care application in the set of matching health care applications is a disease.

13. The method of claim 1, wherein the clinical indication of a health care application in the set of matching health care applications is an allergy a cancer, a disorder of the brain or nervous system, an eye disorder, an ear disorder, or a heart or circulation disorder.

14. The method of claim 1, wherein the clinical indication of a health care application in the set of matching health care applications is a blood disorder, a disorder of the urinary tract, a hormonal disorder, a muscle disorder, a bone disorder, or a joint disorder.

15. The method of claim 1, wherein the evidence score for a respective health care application in the plurality of health care applications is based upon an evaluation, by a medical practitioner, of the efficacy of the respective health care application through a clinical trial.

16. A non-transitory computer readable storage medium for identifying one or more health care applications, wherein the non-transitory computer readable storage medium stores instructions, which when executed by a computer system, cause the computer system to, for each respective user in a plurality of users:
display, at a remote client device associated with the respective user, an application distribution module (204) comprising a plurality of health care applications, wherein each respective health care application in the plurality of health care applications is (i) for a clinical indication and (ii) includes an evidence score that is generated by a plurality of health care providers and not end users;
access, from a user profile database (230) stored in electronic form, a respective user profile (232) associated with the respective user, the user profile comprising:
(i) a set of favorite health care applications (234) for the respective user, selected from the plurality of health care applications,
(ii) a set of prescribed health care applications (236) selected from the plurality of health care applications, wherein each respective prescribed health care application in the set of prescribed health care applications has been prescribed, by the user, to a respective one or more patients in a plurality of patients associated with the user, and
(iii) for each respective prescribed health care application in the set of prescribed health care applications, an application prescription history (238) comprising an identity of each patient in the respective one or more patients to which the respective health care application has been prescribed;
identify one or more health care applications, including:
receiving a search request from the respective user at the remote client device, wherein the search request comprises an alphanumeric query and a set of filtering criteria;
searching, at a health care application venue (206) that tracks the plurality of health care applications, the plurality of health care applications to identify one or more health care applications in the plurality of health care applications that (i) satisfy each respective filtering criterion in the set of filtering criteria and (ii) match the alphanumeric query, thereby identifying a set of matching health care applications, wherein the set of filtering criteria (i) includes an indication that the evidence score of each respective health care application in the set of matching health care applications is to exceed a minimum threshold value and (ii) provides a value for this minimum threshold value;
format for display a search query response, wherein the search query response includes an identification of each respective health care application in the set of matching health care applications, and wherein the formatting includes (i) sorting the set of matching health care applications by a plurality of sorting criteria thereby forming a sorted list of matching health care applications, wherein at least a portion of the sorting criteria is based upon the evidence score of each respective health care application in the set of matching health care applications, and (ii) placing each health care application in the set of matching health care applications that is also in the set of prescribed health care applications at the beginning of the sorted list of matching health care applications;

communicate the search query response including the sorted list of matching health care applications to the remote client device for display;

receive a prescription request from the respective user at the remote client device via user selection of an affordance in the search query response, the prescription request comprising (i) an identification of a first health care application in the sorted list of matching health care applications from the respective user at the remote client device and (ii) an identification of a first patient in the plurality of patients associated with the respective user;

responsive to receiving the prescription request, send an invitation to use the first health care application to an electronic address associated with the first patient, thereby prescribing the first health care application to the first patient; and responsive to receiving a prescription history request from the respective user at the remote client device:

obtain the set of prescribed health care applications from the respective user profile associated with the user; and communicate the set of prescribed health care applications to the remote client device for display, wherein each respective prescribed health care application in the displayed set of prescribed health care applications is sortable by at least an indication, for each respective patient in the respective one or more patients, that the respective health care application was downloaded by the patient.

17. A computer system, comprising:

one or more processors;

memory; and one or more programs stored in the memory for execution by the one or more processors, the one or more programs comprising instructions for, for each respective user in a plurality of users:

displaying, at a remote client device associated with the respective user, an application distribution module (204) comprising a plurality of health care applications, wherein each respective health care application in the plurality of health care applications is (i) for a clinical indication and (ii) includes an evidence score that is generated by a plurality of health care providers and not end users;

accessing, from a user profile database (230) stored in electronic form, a respective user profile (232) associated with the respective user, the user profile comprising:

(i) a set of favorite health care applications (234) for the respective user, selected from the plurality of health care applications, (ii) a set of prescribed health care applications (236) selected from the plurality of health care applications, wherein each respective prescribed health care application in the set of prescribed health care applications has been prescribed, by the user, to a respective one or more patients in a plurality of patients associated with the user, and (iii) for each respective prescribed health care application in the set of prescribed health care applications, an application prescription history (238) comprising an identity of each patient in the respective one or more patients to which the respective health care application has been prescribed;

receiving a search request from the respective user at the remote client device, wherein the search request comprises an alphanumeric query and a set of filtering criteria;

searching, at a health care application venue (206) that tracks the plurality of health care applications, the plurality of health care applications to identify one or more health care applications in the plurality of health care applications that (i) satisfy each respective filtering criterion in the set of filtering criteria and (ii) match the alphanumeric query, thereby identifying a set of matching health care applications, wherein the set of filtering criteria (i) includes an indication that the evidence score of each respective health care application in the set of matching health care applications is to exceed a minimum threshold value and (ii) provides a value for this minimum threshold value;

formatting for display a search query response, wherein the search query response includes an identification of each respective health care application in the set of matching health care applications, and wherein the formatting includes (i) sorting the set of matching health care applications by a plurality of sorting criteria thereby forming a sorted list of matching health care applications, wherein at least a portion of the sorting criteria is based upon the evidence score of each respective health care application in the set of matching health care applications, and (ii) placing each health care application in the set of matching health care applications that is also in the set of prescribed health care applications at the beginning of the sorted list of matching health care applications;

communicating the search query response including the sorted list of matching health care applications to the remote client device for display;

receiving a prescription request from the respective user at the remote client device via user selection of an affordance in the search query response, the prescription request comprising (i) an identification of a first health care application in the sorted list of matching health care applications from the respective user at the remote client device and (ii) an identification of a first patient in the plurality of patients associated with the respective user;

responsive to receiving the prescription request, sending an invitation to use the first health care application to an electronic address associated with the first patient, thereby prescribing the first health care application to the first patient; and responsive to receiving a prescription history request from the respective user at the remote client device:

obtaining the set of prescribed health care applications from the respective user profile associated with the respective user; and communicating set of prescribed health care applications to the remote client device for display, wherein each respective prescribed health care application in the displayed set of prescribed health care applications is sortable by at least an indication, for each respective patient in the respective one or more patients, that the respective health care application was downloaded by the patient.

* * * * *